United States Patent
Tomioka et al.

(10) Patent No.: US 9,523,911 B2
(45) Date of Patent: *Dec. 20, 2016

(54) RADIATION-SENSITIVE RESIN COMPOSITION, RESIST PATTERN-FORMING METHOD, ACID GENERATOR AND COMPOUND

(71) Applicant: JSR CORPORATION, Tokyo (JP)

(72) Inventors: Hiroshi Tomioka, Tokyo (JP); Takakazu Kimoto, Tokyo (JP); Yusuke Asano, Tokyo (JP)

(73) Assignee: JSR CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/282,270

(22) Filed: May 20, 2014

(65) Prior Publication Data

US 2014/0342288 A1  Nov. 20, 2014

(30) Foreign Application Priority Data

May 20, 2013  (JP) ................................. 2013-106643
May 13, 2014  (JP) ................................. 2014-099950

(51) Int. Cl.
C07C 25/18 (2006.01)
C07C 381/12 (2006.01)
C07C 309/04 (2006.01)
G03F 7/039 (2006.01)
G03F 7/004 (2006.01)
C07C 309/17 (2006.01)
G03F 7/11 (2006.01)
G03F 7/20 (2006.01)

(52) U.S. Cl.
CPC ............. *G03F 7/0045* (2013.01); *C07C 25/18* (2013.01); *C07C 309/04* (2013.01); *C07C 309/17* (2013.01); *C07C 381/12* (2013.01); *G03F 7/0046* (2013.01); *G03F 7/0397* (2013.01); *G03F 7/11* (2013.01); *G03F 7/2041* (2013.01)

(58) Field of Classification Search
None
See application file for complete search history.

(56) References Cited

U.S. PATENT DOCUMENTS

| 4,910,122 A | 3/1990 | Arnold et al. | |
| 7,923,199 B2* | 4/2011 | Wada | G03F 7/0045 430/311 |
| 2002/0102491 A1* | 8/2002 | Kodama | C07C 309/06 430/270.1 |
| 2003/0044717 A1* | 3/2003 | Kodama | G03F 7/0045 430/270.1 |
| 2005/0238992 A1* | 10/2005 | Kodama | 430/270.1 |
| 2008/0153030 A1* | 6/2008 | Kobayashi | G03F 7/0397 430/270.1 |
| 2010/0075257 A1* | 3/2010 | Takemoto et al. | 430/286.1 |
| 2011/0117499 A1* | 5/2011 | Matsumiya | C09D 133/16 430/285.1 |
| 2012/0094235 A1* | 4/2012 | Tsuchihashi et al. | 430/285.1 |
| 2012/0282548 A1* | 11/2012 | Enomoto | G03F 7/0045 430/284.1 |
| 2013/0101936 A1* | 4/2013 | Taniguchi | G03F 7/0045 430/280.1 |
| 2013/0149644 A1* | 6/2013 | Maruyama | 430/270.1 |
| 2014/0212808 A1* | 7/2014 | Funatsu | G03F 7/038 430/270.1 |
| 2015/0004545 A1* | 1/2015 | Namai | C07D 307/93 430/285.1 |
| 2016/0011513 A1* | 1/2016 | Kiridoshi | G03F 7/30 430/322 |

FOREIGN PATENT DOCUMENTS

| JP | 59-93448 A | 5/1984 |
| JP | 6-12452 B2 | 2/1994 |
| JP | 8-146610 A | 6/1996 |
| JP | 11-125907 A | 5/1999 |
| JP | 2000-298347 A | 10/2000 |
| JP | 2002-139838 | * 5/2002 |
| JP | 2002-202608 | * 7/2002 |
| JP | 2003-005376 | * 1/2003 |
| JP | 2003-233186 | * 8/2003 |
| JP | 2004-037978 | * 2/2004 |
| JP | 2004-069981 | * 3/2004 |
| JP | 2005-077811 | * 3/2005 |
| JP | 2006-227632 A | 8/2006 |
| WO | WO 2005/069076 A1 | 7/2005 |
| WO | WO 2006/035790 A1 | 4/2006 |

* cited by examiner

*Primary Examiner* — Martin Angebranndt
(74) *Attorney, Agent, or Firm* — Oblon, McClelland, Maier & Neustadt, L.L.P.

(57) ABSTRACT

The present invention provides a radiation-sensitive resin composition that contains a polymer having a structural unit that includes an acid-labile group; and an acid generator, wherein the acid generator includes a compound including a sulfonate anion having $SO_3^-$, wherein a hydrogen atom or an electron-donating group bonds to an α carbon atom with respect to $SO_3^-$, and an electron-withdrawing group bonds to a β carbon atom with respect to $SO_3^-$; and a radiation-degradable onium cation. The compound preferably has a group represented by the following formula (1-1) or (1-2). In the following formulae (1-1) and (1-2), $R^1$ and $R^2$ each independently represent a hydrogen atom or a monovalent electron-donating group. $R^3$ represent a monovalent electron-withdrawing group. $R^4$ represents a hydrogen atom or a monovalent hydrocarbon group.

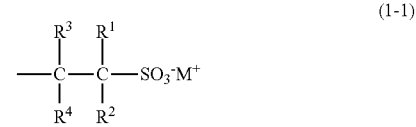

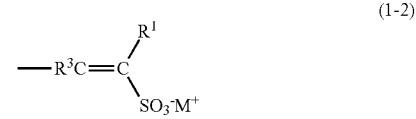

13 Claims, No Drawings

RADIATION-SENSITIVE RESIN COMPOSITION, RESIST PATTERN-FORMING METHOD, ACID GENERATOR AND COMPOUND

CROSS-REFERENCE TO RELATED APPLICATIONS

The present application claims priority to Japanese Patent Application No. 2013-106643, filed May 20, 2013, and to Japanese Patent Application No. 2014-99950, filed May 13, 2014. The contents of these applications are incorporated herein by reference in their entirety.

BACKGROUND OF THE INVENTION

Field of the Invention

The present invention relates to a radiation-sensitive resin composition, a resist pattern-forming method, an acid generator and a compound.

Discussion of the Background

In radiation-sensitive resin compositions for use in microfabrication by lithography, an acid is generated at light-exposed sites upon irradiation with far ultraviolet rays such as an ArF excimer laser beam and a KrF excimer laser beam, charged particle rays such as electron beams, and the like, and chemical reactions catalyzed by the acid make the difference between the rates of dissolution at light-exposed sites and at light-unexposed sites of a resist film in a developer solution, thereby enabling a resist pattern to be formed on a substrate.

For such radiation-sensitive resin compositions, an improvement of resolving ability and rectangularity of a cross-sectional shape of a resist pattern has been demanded with the advance of microfabrication technologies. To address the demand, the type and/or the molecular structure of polymers, acid generating agents and other components for use in the composition have been investigated, and a combination thereof also further investigated in detail (see Japanese Unexamined Patent Application, Publication Nos. H11-125907, H8-146610 and 2000-298347).

In such a current situation in which miniaturization of resist patterns has been further in progress, not only superior rectangularity of a cross-sectional shape and superior resolving ability as described above, but also superior line width roughness (LWR) performances, in which LWR is indicative of variations of line widths in a resist pattern, are demanded. However, the aforementioned conventional radiation-sensitive resin compositions are incapable of meeting these demands.

SUMMARY OF THE INVENTION

The present invention was made in view of the foregoing circumstances, and an object of the present invention is to provide a radiation-sensitive resin composition that exhibits superior LWR performance.

According to an aspect of the invention made for solving the aforementioned problems, a radiation-sensitive resin composition is provided, containing:

a polymer having a structural unit that includes an acid-labile group (hereinafter, may be also referred to as "polymer (A)"); and an acid generator (hereinafter, may be also referred to as "acid generator (B)"), wherein the acid generator includes a compound comprising:

a sulfonate anion having $SO_3^-$, wherein a hydrogen atom or an electron-donating group bonds to an α carbon atom with respect to $SO_3^-$, and an electron-withdrawing group bonds to a β carbon atom with respect to $SO_3^-$; and a radiation-degradable onium cation.

According to another aspect of the present invention, a resist pattern-forming method is provided, including:

providing a resist film using the radiation-sensitive resin composition according to the aspect of the present invention;

exposing the resist film; and developing the exposed resist film.

According to still another aspect of the present invention, an acid generator is provided, including a compound that includes:

a sulfonate anion having $SO_3^-$, wherein a hydrogen atom or an electron-donating group bonds to an α carbon atom with respect to $SO_3^-$, and an electron-withdrawing group bonds to a β carbon atom with respect to $SO_3^-$; and a radiation-degradable onium cation.

According to yet still another aspect of the present invention, a compound is provided, including:

a sulfonate anion having $SO_3^-$, wherein a hydrogen atom or an electron-donating group bonds to an α carbon atom with respect to $SO_3^-$, and an electron-withdrawing group bonds to a β carbon atom with respect to $SO_3^-$; and a radiation-degradable onium cation.

EFFECTS OF THE INVENTION

The radiation-sensitive resin composition and the resist pattern according to the aspects of the present invention enable a resist pattern with reduced LWR to be formed. The acid generator according to the aspect of the present invention can be suitably used as a component of a radiation-sensitive resin composition and improve the LWR performance of the radiation-sensitive resin composition. The compound according to the aspect of the present invention can be suitably used as the acid generator. Therefore, the radiation-sensitive resin composition, the resist pattern, the acid generator and the compound can be suitably used in lithography steps of processes for production of semiconductors and the like, in which further progress of miniaturization is expected in the future.

DESCRIPTION OF EMBODIMENTS

Radiation-Sensitive Resin Composition

A radiation-sensitive resin composition according to an embodiment of the present invention contains (A) a polymer and (B) an acid generator. The radiation-sensitive resin composition may also contain, as favorable components, (C) an acid diffusion controller, (D) a fluorine atom-containing polymer (hereinafter, may be also referred to as "polymer (D)") and (E) a solvent, and further may contain other optional component within a range not leading to impairment of the effects of the present invention. Hereinafter, each component will be explained.

(A) Polymer

The polymer (A) is a polymer having a structural unit that includes an acid-labile group (hereinafter, may be also referred to as "structural unit (I)"). The term "acid-labile group" as referred to means a group that substitutes a hydrogen atom included in a carboxy group, a phenolic hydroxyl group or the like and that is dissociated by an action of an acid. In the radiation-sensitive resin composition according to the embodiment of the present invention, when the polymer (A) has the structural unit (I), the radiation-sensitive resin composition exhibits superior pattern formability.

The polymer (A) preferably has, in addition to the structural unit (I), a structural unit (II) that includes a lactone structure, a cyclic carbonate structure, a sultone structure or a combination thereof and may have a structural unit other than the structural units (I) and (II). The lactone structure, the cyclic carbonate structure and the sultone structure will be described later. Hereinafter, each structural unit will be explained.

Structural Unit (I)

The structural unit (I) is a structural unit that includes an acid-labile group. The structural unit (I) is not particularly limited as long as an acid-labile group is included, and examples thereof include structural units derived from acid-labile group esters of unsaturated carboxylic acids, structural units derived from acid-labile group esters of hydroxystyrenes, and the like. A structural unit represented by the following formula (4) (hereinafter, may be also referred to as "structural unit (I-1)") is preferred in light of an improvement of the pattern formability of the radiation-sensitive resin composition.

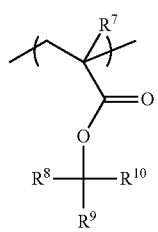

(4)

In the above formula (4), $R^7$ represents a hydrogen atom, a fluorine atom, a methyl group or a trifluoromethyl group; $R^8$ represents a monovalent hydrocarbon group having 1 to 20 carbon atoms; $R^9$ and $R^{10}$ each independently represent a monovalent linear hydrocarbon group having 1 to 10 carbon atoms or a monovalent alicyclic hydrocarbon group having 3 to 20 carbon atoms, wherein $R^9$ and $R^{10}$ optionally taken together represent an alicyclic structure having 3 to 20 carbon atoms together with the carbon atom to which they bond.

$R^7$ represents preferably a hydrogen atom or a methyl group, and more preferably a methyl group in light of the copolymerizability of a monomer that gives the structural unit (I).

Examples of the monovalent hydrocarbon group having 1 to 20 carbon atoms which may be represented by $R^8$ include linear hydrocarbon groups having 1 to 10 carbon atoms, monovalent alicyclic hydrocarbon groups having 3 to 20 carbon atoms, monovalent aromatic hydrocarbon groups having 6 to 20 carbon atoms, and the like.

Examples of the linear hydrocarbon group having 1 to 10 carbon atoms which may be represented by $R^8$ to $R^{10}$ include:

alkyl groups such as a methyl group, an ethyl group, a n-propyl group, an i-propyl group, a n-butyl group, a 2-methylpropyl group, a 1-methylpropyl group and a t-butyl group;

alkenyl groups such as an ethenyl group, a propenyl group and a butenyl group;

alkynyl group such as an ethynyl group, a propynyl group and a butynyl group; and the like.

Examples of the alicyclic hydrocarbon group having 3 to 20 carbon atoms which may be represented by $R^8$ to $R^{10}$ include:

monocyclic cycloalkyl groups such as a cyclopropyl group, a cyclobutyl group, a cyclopentyl group and a cyclohexyl group;

polycyclic cycloalkyl groups such as a norbornyl group, an adamantyl group, a tricyclodecyl group and a tetracyclododecyl group;

cycloalkenyl groups such as a cyclopropenyl group, a cyclobutenyl group, a cyclopentenyl group and a cyclohexenyl group;

polycyclic cycloalkenyl groups such as a norbornenyl group, a tricyclodecenyl group and a tetracyclododecenyl group; and the like.

Examples of the monovalent aromatic hydrocarbon group having 6 to 20 carbon atoms which may be represented by $R^8$ include:

aryl groups such as a phenyl group, a tolyl group, a xylyl group, a naphthyl group and an anthryl group;

aralkyl groups such as a benzyl group, a phenethyl group and a naphthylmethyl group; and the like.

$R^8$ preferably represents a linear hydrocarbon group having 1 to 10 carbon atoms or a monovalent alicyclic hydrocarbon group having 3 to 20 carbon atoms.

Examples of the alicyclic structure having 3 to 20 carbon atoms which may be represented by the linear hydrocarbon group or the alicyclic hydrocarbon group which may be represented by $R^9$ and the linear hydrocarbon group or the alicyclic hydrocarbon group which may be represented by $R^{10}$ taken together with the carbon atom to which they bond include:

monocyclic cycloalkane structures such as a cyclopropane structure, a cyclobutane structure, a cyclopentane structure, a cyclohexane structure, a cycloheptane structure and a cyclooctane structure;

monocyclic cycloalkene structures such as a cyclopentene structure and a cyclohexene structure;

polycyclic cycloalkane structures such as a norbornane structure, an adamantane structure, a tricyclodecane structure and a tetracyclododecane structure;

polycyclic cycloalkene structures such as a norbornene structure and a tricyclodecene structure; and the like.

Among these, monocyclic and polycyclic cycloalkane structures are preferred.

Among these, it is preferred that $R^8$ represents an alkyl group having 1 to 4 carbon atoms, and the alicyclic structure which may be represented by $R^9$ and $R^{10}$ taken together with the carbon atom to which they bond is a polycyclic or monocyclic cycloalkane structure.

Examples of the structural unit (I-1) include structural units represented by the following formulae (4-1) to (4-4) (hereinafter, may be also referred to as "structural units (I-1-1) to (I-1-4)"), and the like.

(4-1) 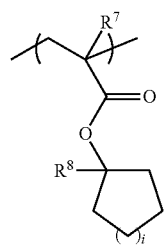
(4-2) 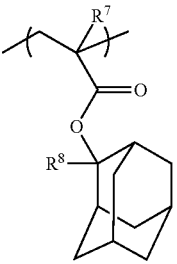
(4-3) 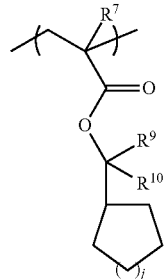
(4-4) 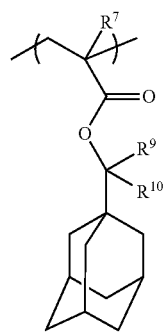
In the above formulae (4-1) to (4-4), $R^7$ to $R^{10}$ are as defined in the above formula (4); and i and j are each independently an integer of 1 to 4.
Further, i and j are preferably 1.
Examples of the structural units (I-1-1) to (I-1-4) include structural units represented by the following formulae, and the like.
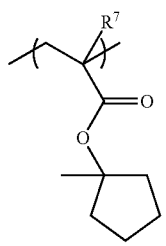 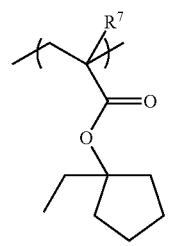 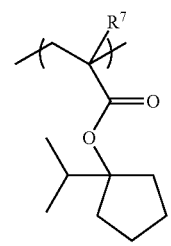
-continued
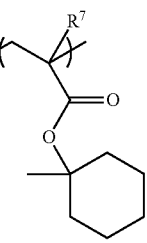 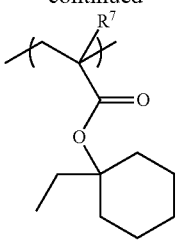 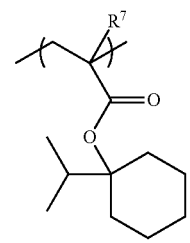
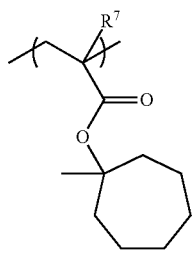 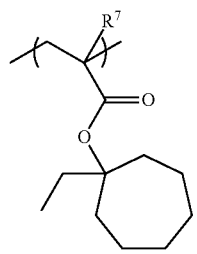
 
 
 
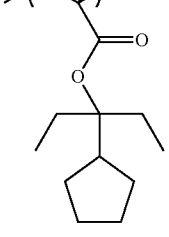 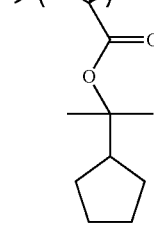 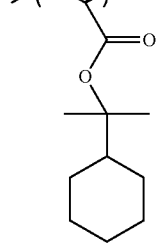

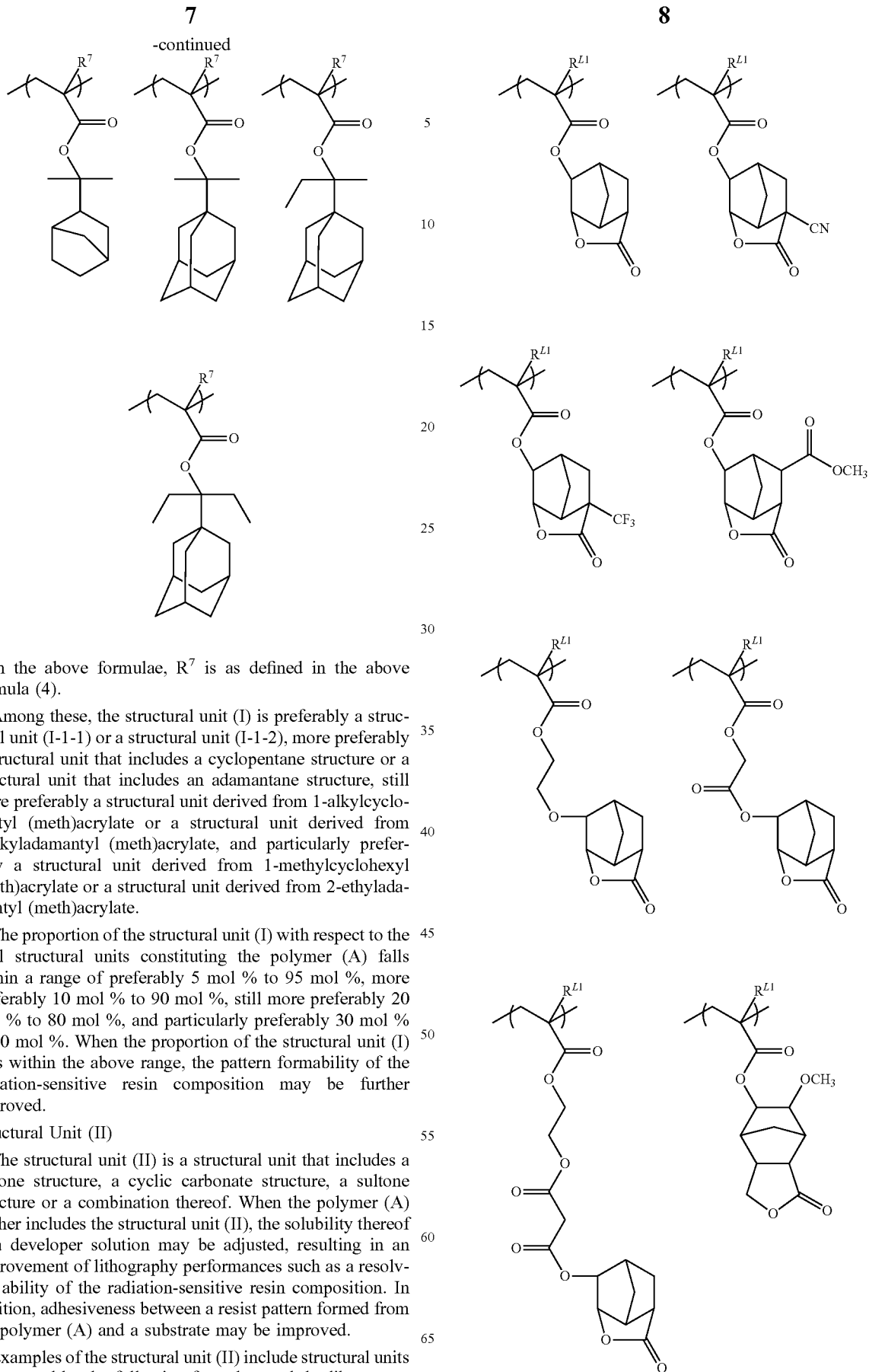

In the above formulae, $R^7$ is as defined in the above formula (4).

Among these, the structural unit (I) is preferably a structural unit (I-1-1) or a structural unit (I-1-2), more preferably a structural unit that includes a cyclopentane structure or a structural unit that includes an adamantane structure, still more preferably a structural unit derived from 1-alkylcyclopentyl (meth)acrylate or a structural unit derived from 2-alkyladamantyl (meth)acrylate, and particularly preferably a structural unit derived from 1-methylcyclohexyl (meth)acrylate or a structural unit derived from 2-ethyladamantyl (meth)acrylate.

The proportion of the structural unit (I) with respect to the total structural units constituting the polymer (A) falls within a range of preferably 5 mol % to 95 mol %, more preferably 10 mol % to 90 mol %, still more preferably 20 mol % to 80 mol %, and particularly preferably 30 mol % to 70 mol %. When the proportion of the structural unit (I) falls within the above range, the pattern formability of the radiation-sensitive resin composition may be further improved.

Structural Unit (II)

The structural unit (II) is a structural unit that includes a lactone structure, a cyclic carbonate structure, a sultone structure or a combination thereof. When the polymer (A) further includes the structural unit (II), the solubility thereof in a developer solution may be adjusted, resulting in an improvement of lithography performances such as a resolving ability of the radiation-sensitive resin composition. In addition, adhesiveness between a resist pattern formed from the polymer (A) and a substrate may be improved.

Examples of the structural unit (II) include structural units represented by the following formulae, and the like.

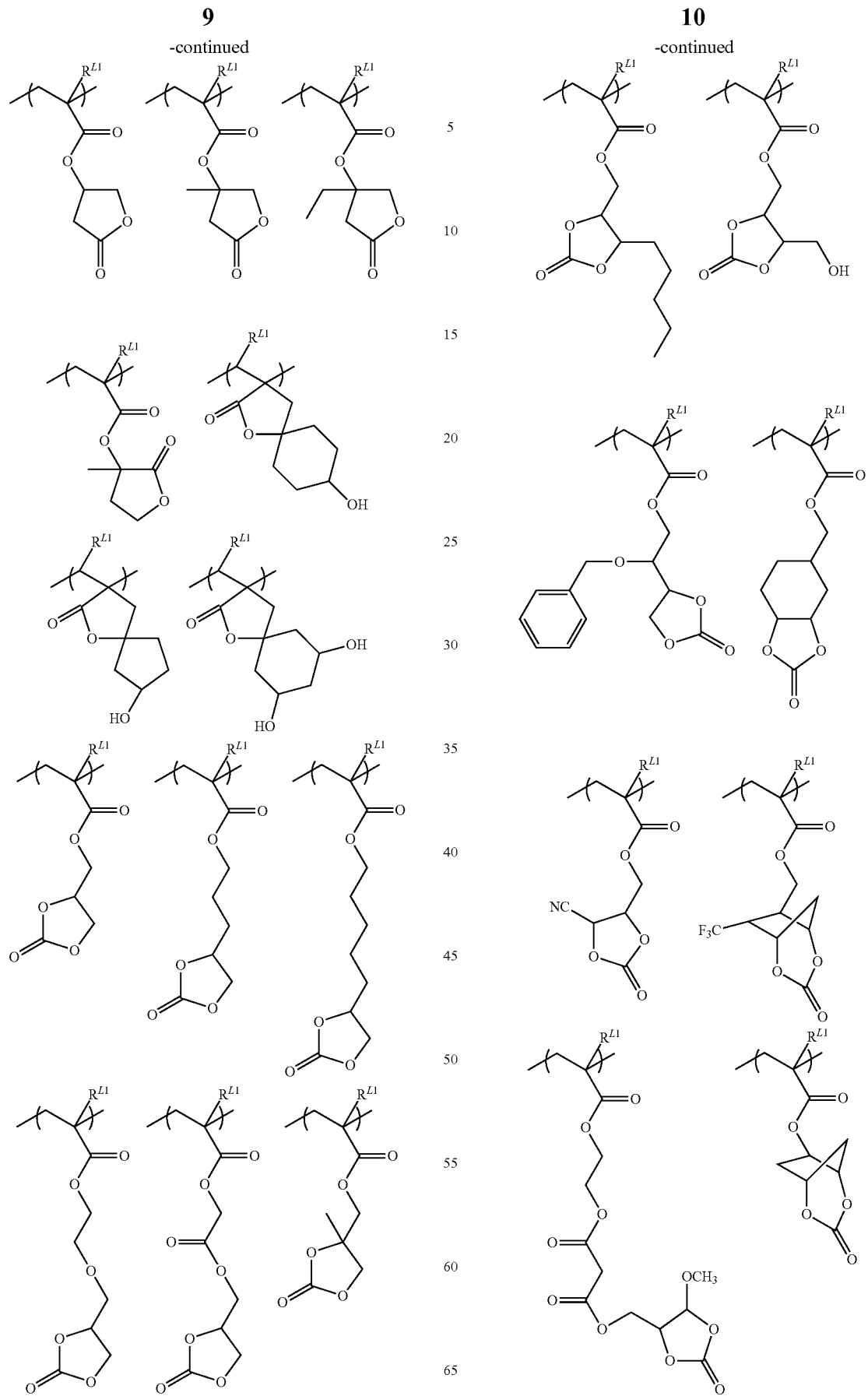

-continued

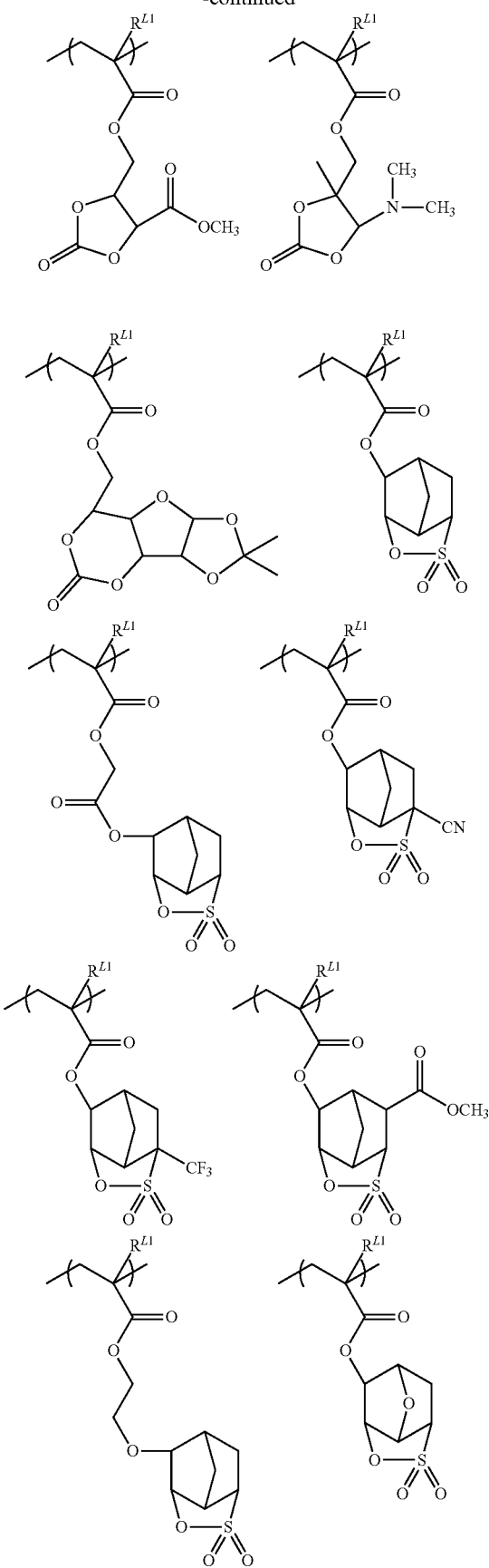

-continued

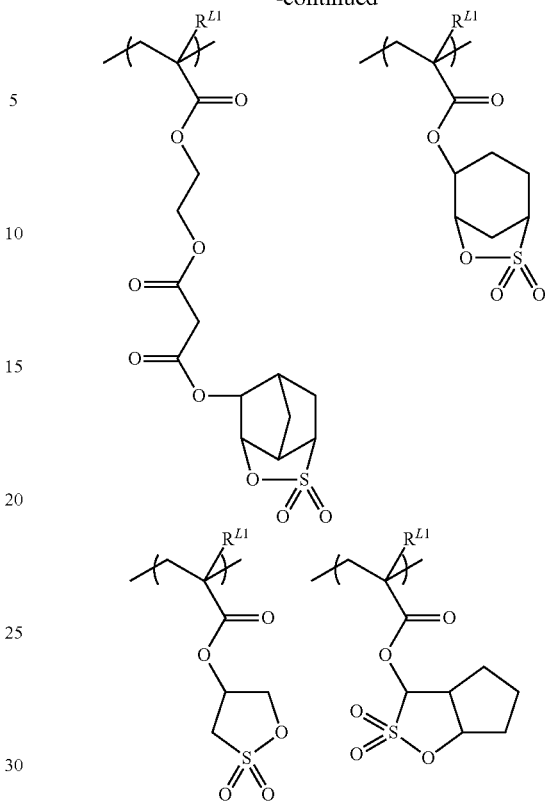

In the above formulae, $R^{L1}$ represents a hydrogen atom, a fluorine atom, a methyl group or a trifluoromethyl group.

Among these, the structural unit (II) is preferably a structural unit that includes a lactone structure, more preferably a structural unit that includes a norbornanelactone structure, and still more preferably a structural unit derived from a norbornanelacton-yl (meth)acrylate.

The proportion of the structural unit (II) with respect to the total structural units constituting the polymer (A) falls within a range of preferably 20 mol % to 80 mol %, more preferably 25 mol % to 70 mol %, and still more preferably 30 mol % to 60 mol %. When the proportion of the structural unit (II) falls within the above range, a further improvement of lithography performances such as a resolving ability of the radiation-sensitive resin composition and adhesiveness of the resultant resist pattern to a substrate may be attained.

Other Structural Unit

The polymer (A) may have other structural unit in addition to the structural units (I) and (II). Examples of the other structural unit include a structural unit that includes a polar group, and the like (except for the structural unit falling under the structural unit (II)). When the polymer (A) further has the structural unit that includes a polar group, the solubility of the polymer (A) in a developer solution can be adjusted, resulting in an improvement of lithography performances such as a resolving ability of the radiation-sensitive resin composition. Examples of the polar group include a hydroxy group, a carboxy group, a cyano group, a nitro group, a sulfonamide group, and the like. Among these, a hydroxy group and a carboxy group are preferred, and a hydroxy group is more preferred.

Examples of the structural unit that includes a polar group include structural units represented by the following formulae, and the like.

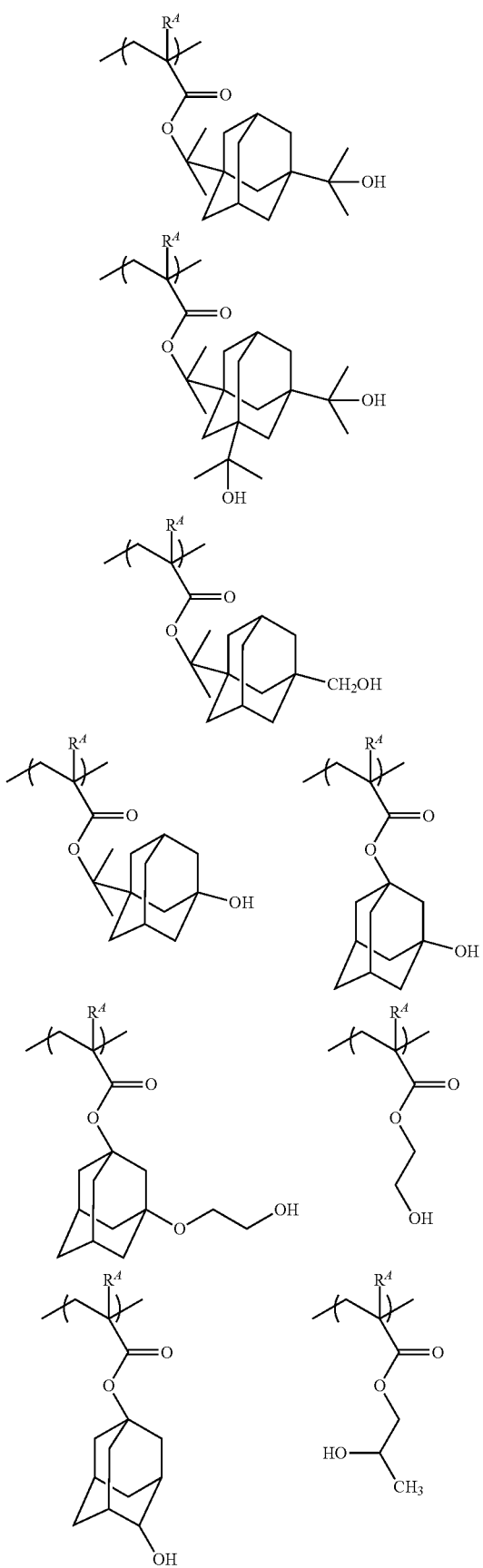
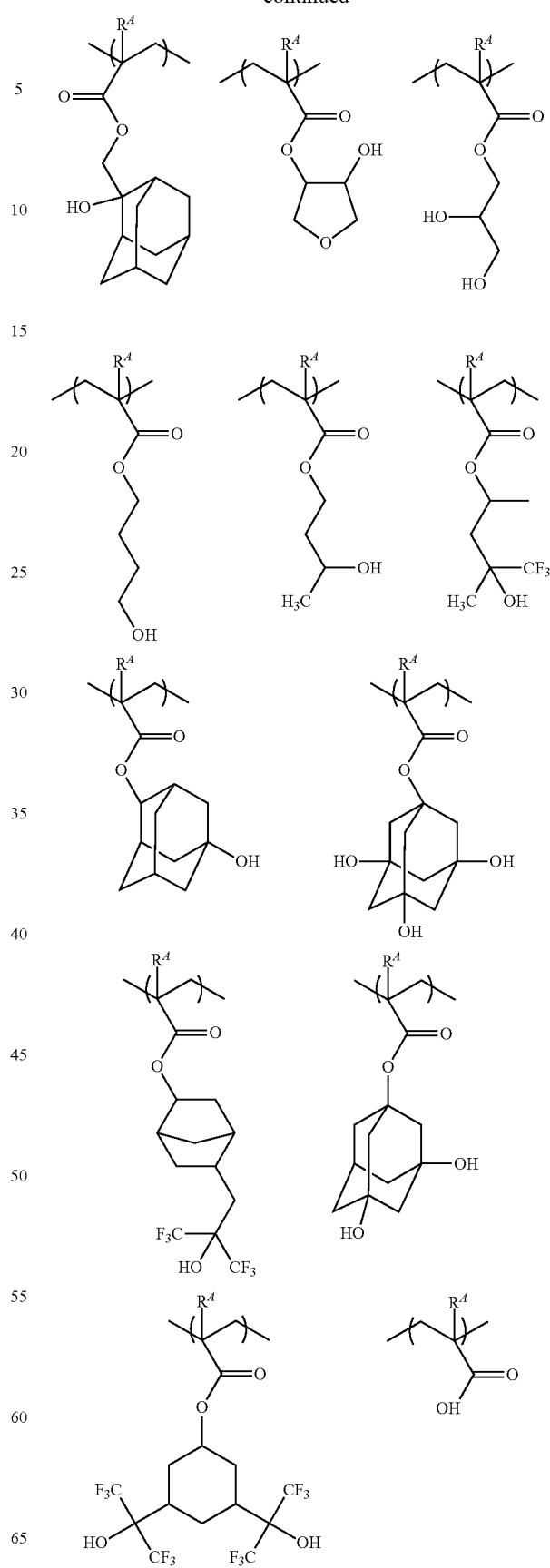

-continued

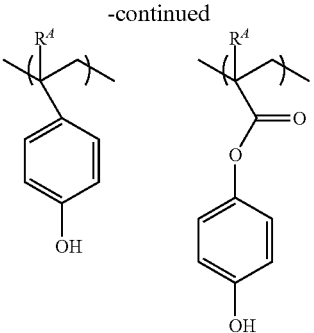

In the above formulae, $R^A$ represents a hydrogen atom, a fluorine atom, a methyl group or a trifluoromethyl group.

The proportion of the structural unit that includes a polar group with respect to the total structural units constituting the polymer (A) falls within a range of preferably 0 mol % to 40 mol %, more preferably 0 mol % to 30 mol %, and still more preferably 0 mol % to 20 mol %. When the proportion of the structural unit that includes a polar group falls within the above range, lithography performances such as a resolving ability of the radiation-sensitive resin composition may be further improved.

The polymer (A) may have a structural unit other than the structural unit that includes a polar group as the other structural unit. The proportion of such a structural unit with respect to the total structural units constituting the polymer (A) is preferably no greater than 30 mol %, and more preferably no greater than 20 mol %.

Method for Synthesis of Polymer (A)

The polymer (A) can be synthesized, for example, by polymerizing monomer(s) that give(s) each structural unit in an appropriate solvent using a radical polymerization initiator and the like.

Examples of the radical polymerization initiator include: azo radical initiators such as azobisisobutyronitrile (AIBN), 2,2'-azobis(4-methoxy-2,4-dimethylvaleronitrile), 2,2'-azobis(2-cyclopropylpropionitrile), 2,2'-azobis(2,4-dimethylvaleronitrile) and dimethyl 2,2'-azobisisobutyrate; peroxide radical initiators such as benzoyl peroxide, t-butyl hydroperoxide and cumene hydroperoxide; and the like. Among these, AIBN and dimethyl 2,2'-azobisisobutyrate are preferred, and AIBN is more preferred. These radical initiators may be used either alone, or as a mixture of two or more types thereof.

Examples of the solvent for use in the polymerization include:
 alkanes such as n-pentane, n-hexane, n-heptane, n-octane, n-nonane and n-decane;
 cycloalkanes such as cyclohexane, cycloheptane, cyclooctane, decalin and norbornane;
 aromatic hydrocarbons such as benzene, toluene, xylene, ethylbenzene and cumene;
 halogenated hydrocarbons such as chlorobutanes, bromohexanes, dichloroethanes, hexamethylene dibromides and chlorobenzene;
 saturated carboxylic acid esters such as ethyl acetate, n-butyl acetate, i-butyl acetate and methyl propionate;
 ketones such as acetone, methyl ethyl ketone, 4-methyl-2-pentanone and 2-heptanone;
 ethers such as tetrahydrofuran, diethoxyethanes and diethoxyethanes;
 alcohols such as methanol, ethanol, 1-propanol, 2-propanol and 4-methyl-2-pentanol; and the like. These solvents for use in the polymerization may be used either alone or in combination of two or more types thereof.

The reaction temperature employed in the polymerization falls within a range of typically 40° C. to 150° C., and preferably 50° C. to 120° C. The reaction time falls within a range of typically 1 hour to 48 hours, and preferably 1 hour to 24 hours.

The polystyrene equivalent weight average molecular weight (Mw) of the polymer (A) as determined by gel permeation chromatography (GPC) is not particularly limited, but falls within a range of preferably no less than 1,000 and no greater than 50,000, more preferably no less than 2,000 and no greater than 30,000, still more preferably no less than 3,000 and no greater than 15,000, and particularly preferably no less than 4,000 and no greater than 12,000. When the Mw of the polymer (A) is less than the lower limit, the heat resistance of the resultant resist film may be deteriorated. When the Mw of the polymer (A) is greater than the upper limit, the developability of the resist film may be impaired.

The ratio (Mw/Mn) of the Mw to the polystyrene equivalent number average molecular weight (Mn) as determined by GPC of the polymer (A) falls within a range of typically no less than 1 and no greater than 5, and preferably no less than 1 and no greater than 3, and still more preferably no less than 1 and no greater than 2.

The Mw and Mn of polymers presented in the present specification are those determined by gel permeation chromatography (GPC) under the following conditions:
 GPC columns: G2000HXL×2, G3000HXL×1, G4000HXL×1 (each manufactured by Tosoh Corporation)
 column temperature: 40° C.
 elution solvent: tetrahydrofuran (manufactured by Wako Pure Chemical Industries, Ltd.)
 flow rate: 1.0 mL/min
 sample concentration: 1.0% by mass
 amount of injected sample: 100 μL
 detector: differential refractometer
 standard substance: mono-dispersed polystyrene The amount of the polymer (A) with respect to the total solid content of the radiation-sensitive resin composition is preferably no less than 70% by mass, more preferably no less than 80% by mass, and still more preferably no less than 85% by mass.

(B) Acid Generator

The acid generator (B) includes a compound (hereinafter, may be also referred to as "compound (I)") that includes a sulfonate anion (hereinafter, may be also referred to as "sulfonate anion (A)") having $SO_3^-$, wherein a hydrogen atom or an electron-donating group bonds to an α carbon atom with respect to $SO_3^-$, and an electron-withdrawing group bonds to a β carbon atom with respect to $SO_3^-$; and a radiation-degradable onium cation. When the radiation-sensitive resin composition contains the acid generator (B), the radiation-sensitive resin composition exhibits superior LWR performance.

Compound (I)

The compound (I) is a compound that includes the sulfonate anion (A) and the radiation-degradable onium cation. Hereinafter, the sulfonate anion (A) and the radiation-degradable onium cation will be explained in this order.

Sulfonate Anion (A)

The sulfonate anion (A) is a sulfonate anion having $SO_3^-$, wherein a hydrogen atom or an electron-donating group bonds to an α carbon atom with respect to $SO_3^-$, and an electron-withdrawing group bonds to a β carbon atom with respect to $SO_3^-$. The term "α carbon atom with respect to $SO_3^-$" as referred to means a carbon atom to which $SO_3^-$ bonds, and the term "β carbon atom with respect to $SO_3^-$" as referred to means a carbon atom adjacent to the α carbon atom. When the compound (I) of the acid generator (B) includes the sulfonate anion (A), the radiation-sensitive resin composition exhibits superior LWR performance. Although the reasons for the fact that the radiation-sensitive resin composition exhibits superior LWR performance when the sulfonate anion (A) includes the aforementioned structure is not necessarily clear, it is presumed, for example, that the absence of the electron-withdrawing group at the α-position and the presence of one electron-withdrawing group at only the β carbon atom in the sulfonate anion (A) permit the acid generator (B) to exhibit more proper acidity, as compared with conventional acid generators, or the like.

The electron-donating group is not particularly limited as long as the electron-donating group more readily donates an electron to the bonded atom as compared with the hydrogen atom; and the electron-donating group may be a monovalent group or a group having a valency of two or more, but a monovalent group is preferred. Moreover, one or two electron-donating group(s) may bond to the α carbon atom.

Examples of the electron-donating group include hydrocarbon groups, a hydroxy group, oxyhydrocarbon groups, oxycarbonyl hydrocarbon groups, an amino group, hydrocarbon-substituted amino groups, hydrocarbon-substituted amide groups, and the like. Among these, hydrocarbon groups, oxyhydrocarbon groups and an amino group are preferred in light of a possible adjustment to give proper acidity of the acid generated from the compound (I).

Examples of the monovalent electron-donating group include —R', —OH, —OR', —OCOR', —NH$_2$, —NR'$_2$, —NHR', —NHCOR' and the like, wherein R' represents a monovalent hydrocarbon group.

Examples of the monovalent hydrocarbon group which may be represented by R' include:
monovalent linear hydrocarbon groups such as alkyl groups such as a methyl group, an ethyl group, a propyl group and a butyl group; alkenyl groups such as an ethenyl group, a propenyl group and a butenyl group; and alkynyl groups such as an ethynyl group, a propynyl group and a butynyl group;
monovalent alicyclic hydrocarbon groups such as cycloalkyl groups such as a cyclopropyl group, a cyclobutyl group, a cyclopentyl group, a cyclohexyl group, a norbornyl group and an adamantyl group; and cycloalkenyl groups such as a cyclopropenyl group, a cyclobutenyl group, a cyclopentenyl group and a norbornenyl group;
monovalent aromatic hydrocarbon groups such as aryl groups such as a phenyl group, a tolyl group, a xylyl group, a mesityl group, a naphthyl group, a methylnaphthyl group, an anthryl group and a methylanthryl group; and aralkyl groups such as a benzyl group, a phenethyl group, a phenylpropyl group, a naphthylmethyl group and an anthrylmethyl group; and the like.

Among these, the monovalent electron-donating group is preferably —R', —OR', —NH$_2$, —NHR' and —NR'$_2$, more preferably —R' (monovalent hydrocarbon group), still more preferably a monovalent linear hydrocarbon group, yet still more preferably an alkyl group, and particularly preferably a methyl group in light of a possible adjustment to give more proper acidity of the acid generated from the compound (I).

The group or atom that bonds to the α carbon atom is preferably a hydrogen atom in light of the ease in synthesis of the compound (I).

The electron-withdrawing group is not particularly limited as long as the electron-withdrawing group more readily attracts an electron group from the bonded atom as compared with the hydrogen atom; and the electron-withdrawing group may be a monovalent group or a group having a valency of two or more, but a monovalent group is preferred. One electron-withdrawing group bonds to the β carbon atom.

Examples of the electron-withdrawing group include halogen atoms such as a fluorine atom, a chlorine atom, a bromine atom and an iodine atom, halogenated hydrocarbon groups, a nitro group, a cyano group, a formyl group, carbonyl hydrocarbon groups, carbonyloxy hydrocarbon groups, sulfonyl hydrocarbon groups, a carboxy group, a sulfo group, and the like. Among these, a cyano group, halogen atoms and halogenated hydrocarbon groups are preferred in light of the ease in synthesis of the compound (I), a cyano group, a fluorine atom and fluorinated hydrocarbon groups are more preferred in light of a possible adjustment to give more proper acidity of the acid generated from the compound (I), a fluorine atom and fluorinated hydrocarbon groups are still more preferred, and fluorinated hydrocarbons are particularly preferred.

Examples of the monovalent electron-withdrawing group include halogen atoms, monovalent halogenated hydrocarbon groups, a nitro group, a cyano group, a formyl group, —COR', —CO$_2$R', —SO$_2$R', a carboxy group, a sulfo group and the like, wherein R' represents a monovalent hydrocarbon group.

Examples of the monovalent halogenated hydrocarbon group include:
monovalent fluorinated hydrocarbon groups including:
monovalent fluorinated linear hydrocarbon groups such as e.g., fluorinated alkyl groups such as a fluoromethyl group, a difluoromethyl group, a trifluoromethyl group, a fluoroethyl group, a difluoroethyl group, a trifluoroethyl group, a pentafluoroethyl group, a trifluoropropyl group, a hexafluoropropyl group, a heptafluoropropyl group and a nonafluorobutyl group;
fluorinated alkenyl groups such as a fluoroethenyl group and a trifluoroethenyl group; and
fluorinated alkynyl groups such as a fluoroethynyl group;
monovalent fluorinated alicyclic hydrocarbon groups such as e.g., fluorinated cycloalkyl groups such as a fluorocyclopentyl group, a perfluorocyclopentyl group, a perfluorocyclohexyl group, a perfluoronorbornyl group and a perfluoroadamantyl group; and
fluorinated cycloalkenyl groups such as a fluorocyclopentenyl group and a difluoronorbornenyl group;
fluorinated aryl groups such as a fluorophenyl group, a difluorophenyl group, a trifluorophenyl group, a pentafluorophenyl group, a fluorotolyl group, a trifluorotolyl group, a fluoronaphthyl group and a fluoroanthryl group; and
fluorinated aralkyl groups such as a fluorobenzyl group, a difluorobenzyl group and a fluoronaphthylmethyl group;
monovalent chlorinated hydrocarbon groups such as a trichloromethyl group, a perchlorocyclohexyl group and a pentachlorophenyl group;
monovalent brominated hydrocarbon groups such as a tribromomethyl group, a perbromocyclohexyl group and a pentabromophenyl group; and
monovalent iodinated hydrocarbon groups such as a triiodomethyl group, a periodocyclohexyl group and a pentaiodophenyl group.

Examples of the monovalent hydrocarbon group which may be represented by R' include the same groups as those exemplified hereinabove as the monovalent hydrocarbon group which may be represented by R', and the like.

Among these, the monovalent electron-withdrawing group is preferably a cyano group, a fluorine atom or a monovalent fluorinated hydrocarbon group, more preferably a fluorine atom or a monovalent fluorinated hydrocarbon group, still more preferably a monovalent fluorinated hydrocarbon group, particularly preferably a perfluoroalkyl group, and further particularly preferably a trifluoromethyl group.

A group other than electron-withdrawing groups may bond to the β carbon atom with respect to $SO_3^-$ of the sulfonate anion (A) in addition to the aforementioned one electron-withdrawing group. Examples of the group other than electron-withdrawing groups include a hydrogen atom, a hydrocarbon group, and the like.

Radiation-Degradable Onium Cation

The radiation-degradable onium cation is a cation that is degraded by irradiation with a radiation. At light-exposed sites, a sulfonic acid is generated from a proton yielded upon the degradation of the radiation-degradable onium cation and the sulfonate anion (A). Examples of the radiation include: electromagnetic radiations such as ultraviolet rays, far ultraviolet rays, extreme-ultraviolet rays (EUV), X-rays and γ rays; charged particle rays such as electron beams and a rays; and the like. Among these, far ultraviolet rays, EUV and electron beams are preferred, far ultraviolet rays are more preferred, a KrF excimer laser beam (248 nm) and an ArF excimer laser beam (193 nm) are still more preferred, and an ArF excimer laser beam is particularly preferred.

Examples of the radiation-degradable onium cation include radiation-degradable onium cations that contain an element such as S, I, O, N, P, Cl, Br, F, As, Se, Sn, Sb, Te or Bi. Among these, sulfonium cations that contain S (sulfur) as the element and iodonium cations that contain I (iodine) as the element are preferred, and a cation represented by the following formula (X-1), a cation represented by the following formula (X-2) and a cation represented by the following formula (X-3) are more preferred.

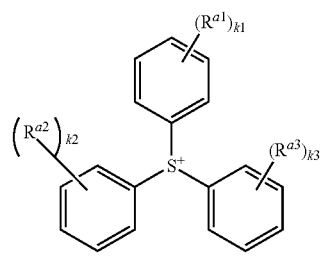
(X-1)

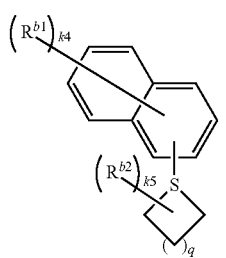
(X-2)

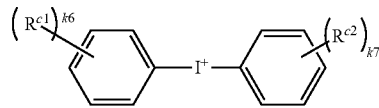
(X-3)

In the above formula (X-1), $R^{a1}$, $R^{a2}$ and $R^{a3}$ each independently represent a substituted or unsubstituted linear or branched alkyl group having 1 to 12 carbon atoms, a substituted or unsubstituted aromatic hydrocarbon group having 6 to 12 carbon atoms, $-OSO_2-R^P$ or $-SO_2-R^Q$, and two or more of the substituted or unsubstituted linear or branched alkyl group having 1 to 12 carbon atoms, the substituted or unsubstituted aromatic hydrocarbon group having 6 to 12 carbon atoms, $-OSO_2-R^P$ and $-SO_2-R^Q$ may taken together represent a ring structure, and the rest of these groups is as defined above; $R^P$ and $R^Q$ each independently represent a substituted or unsubstituted linear or branched alkyl group having 1 to 12 carbon atoms, a substituted or unsubstituted alicyclic hydrocarbon group having 5 to 25 carbon atoms or a substituted or unsubstituted aromatic hydrocarbon group having 6 to 12 carbon atoms; and k1, k2 and k3 is each independently an integer of 0 to 5, wherein in a case where $R^{a1}$ to $R^{a3}$ as well as $R^P$ and $R^Q$ are each present in a plurality of number, a plurality of $R^{a1}$s may be identical or different, a plurality of $R^{a2}$s may be identical or different, a plurality of $R^{a3}$s may be identical or different, a plurality of $R^P$s may be identical or different, and a plurality of $R^Q$s may be identical or different.

In the above formula (X-2), $R^{b1}$ represents a substituted or unsubstituted linear or branched alkyl group having 1 to 8 carbon atoms, or a substituted or unsubstituted aromatic hydrocarbon group having 6 to 8 carbon atoms; k4 is an integer of 0 to 7, wherein in a case where $R^{b1}$ is present in a plurality of number, a plurality of $R^{b1}$s may be identical or different, wherein the plurality of $R^{b1}$s taken together may represent a ring structure; $R^{b2}$ represents a substituted or unsubstituted linear or branched alkyl group having 1 to 7 carbon atoms, or a substituted or unsubstituted aromatic hydrocarbon group having 6 or 7 carbon atoms; k5 is an integer of 0 to 6, wherein in a case where $R^{b2}$ is present in a plurality of number, a plurality of $R^{b2}$s may be identical or different, wherein the plurality of $R^{b2}$s taken together may represent a ring structure; and q is an integer of 0 to 3.

In the above formula (X-3), $R^{c1}$ and $R^{c2}$ each independently represent a substituted or unsubstituted linear or branched alkyl group having 1 to 12 carbon atoms, a substituted or unsubstituted aromatic hydrocarbon group having 6 to 12 carbon atoms, $-OSO_2-R^R$ or $-SO_2-R^S$, and two or more of the substituted or unsubstituted linear or branched alkyl group having 1 to 12 carbon atoms, the substituted or unsubstituted aromatic hydrocarbon group having 6 to 12 carbon atoms, $-OSO_2-R^R$ and $-SO_2-R^S$ taken together represent a ring structure; $R^R$ and $R^S$ each independently represent a substituted or unsubstituted linear or branched alkyl group having 1 to 12 carbon atoms, a substituted or unsubstituted alicyclic hydrocarbon group having 5 to 25 carbon atoms or a substituted or unsubstituted aromatic hydrocarbon group having 6 to 12 carbon atoms; and k6 and k7 is each independently an integer of 0 to 5, wherein in a case where $R^{c1}$, $R^{c2}$, and $R^S$ are each present in a plurality of number, a plurality of $R^{c1}$s may be identical or different, a plurality of $R^{c2}$s may be identical or different, a plurality of $R^R$s may be identical or different, and a plurality of $R^S$s may be identical or different.

Examples of the unsubstituted linear alkyl group which may be represented by $R^{a1}$ to $R^{a3}$, $R^{b1}$, $R^{b2}$, $R^{c1}$ and $R^{c2}$ include a methyl group, an ethyl group, a n-propyl group, a n-butyl group, and the like.

Examples of the unsubstituted branched alkyl group which may be represented by $R^{a1}$ to $R^{a3}$, $R^{b1}$, $R^{b2}$, $R^{c1}$ and $R^{c2}$ include an i-propyl group, an i-butyl group, a sec-butyl group, a t-butyl group, and the like.

Examples of the unsubstituted aromatic hydrocarbon group which may be represented by $R^{a1}$ to $R^{a3}$, $R^c$ and $R^{c2}$ include: aryl groups such as a phenyl group, a tolyl group, a xylyl group, a mesityl group and a naphthyl group; aralkyl groups such as a benzyl group and a phenethyl group; and the like.

Examples of the unsubstituted aromatic hydrocarbon group which may be represented by $R^{b1}$ and $R^{b2}$ include a phenyl group, a tolyl group, a benzyl group, and the like.

Examples of a substituent that may substitute for a hydrogen atom included in the alkyl group and the aromatic hydrocarbon group include halogen atoms such as a fluorine atom, a chlorine atom, a bromine atom and an iodine atom, a hydroxy group, a carboxy group, a cyano group, a nitro group, an alkoxy group, an alkoxycarbonyl group, an alkoxycarbonyloxy group, an acyl group, an acyloxy group, and the like.

Among these, halogen atoms are preferred, and a fluorine atom is more preferred.

$R^{a1}$ to $R^{a3}$, $R^{b1}$, $R^{b2}$, $R^{c1}$ and $R^{c2}$ preferably represent an unsubstituted linear or branched alkyl group, a fluorinated alkyl group, an unsubstituted monovalent aromatic hydrocarbon group, $-OSO_2-R''$ or $-SO_2-R''$, more preferably a fluorinated alkyl group or an unsubstituted monovalent aromatic hydrocarbon group, and still more preferably a fluorinated alkyl group, wherein R" represents an unsubstituted monovalent alicyclic hydrocarbon group or an unsubstituted monovalent aromatic hydrocarbon group.

In the above formula (X-1), k1, k2 and k3 are preferably an integer of 0 to 2, more preferably 0 or 1, and still more preferably 0.

In the above formula (X-2), k4 is preferably an integer of 0 to 2, more preferably 0 or 1, and still more preferably 1; and k5 is preferably an integer of 0 to 2, more preferably 0 or 1, and still more preferably 0.

In the above formula (X-3), k6 and k7 are preferably an integer of 0 to 2, more preferably 0 or 1, and still more preferably 0.

Examples of the sulfonium cation include cations represented by the following formulae (i-1) to (i-67), and the like.

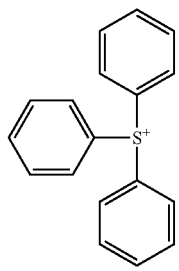

(i-1)

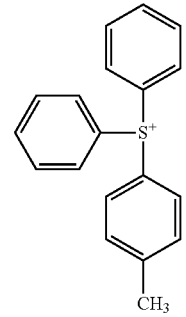

(i-2)

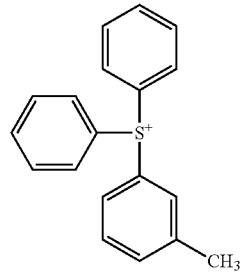

(i-3)

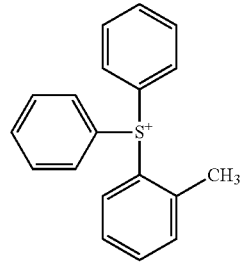

(i-4)

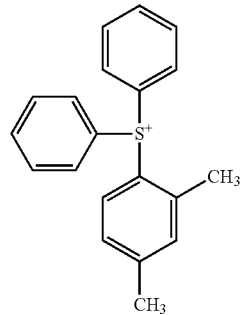

(i-5)

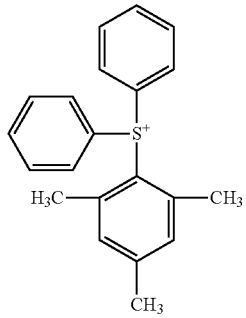

(i-6)

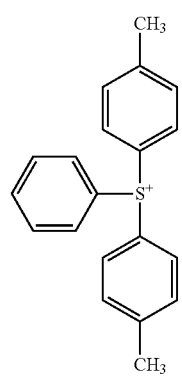 (i-7)
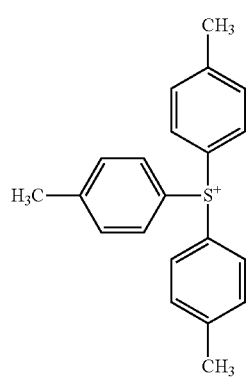 (i-8)
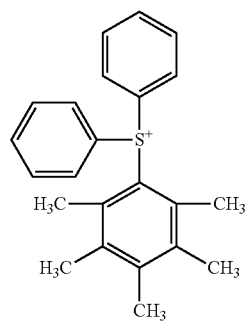 (i-9)
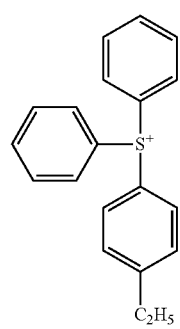 (i-10)
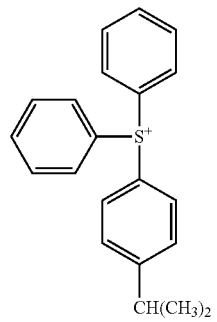 (i-11)
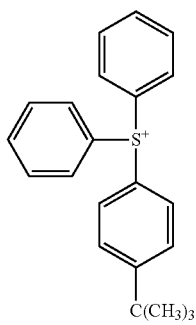 (i-12)
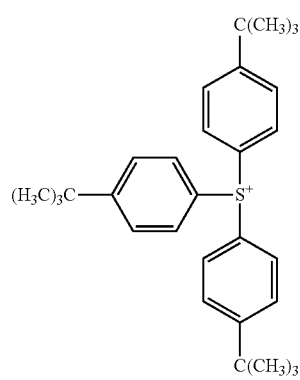 (i-13)
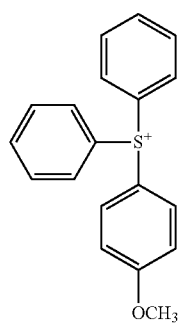 (i-14)

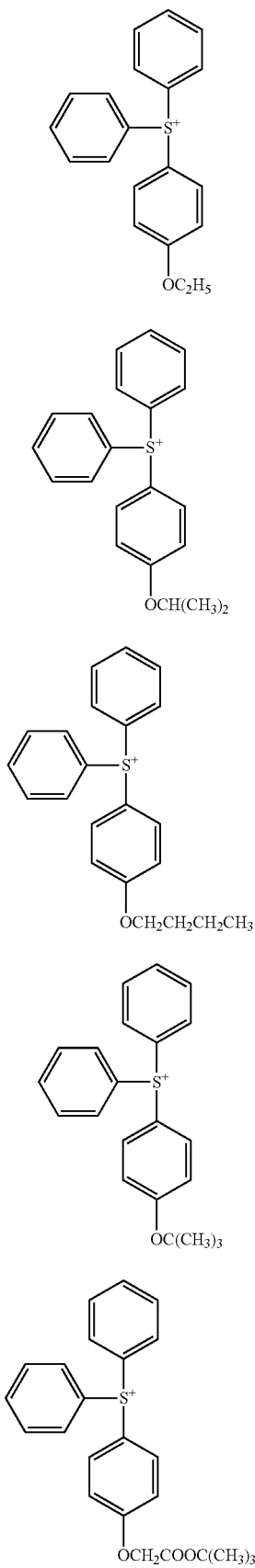
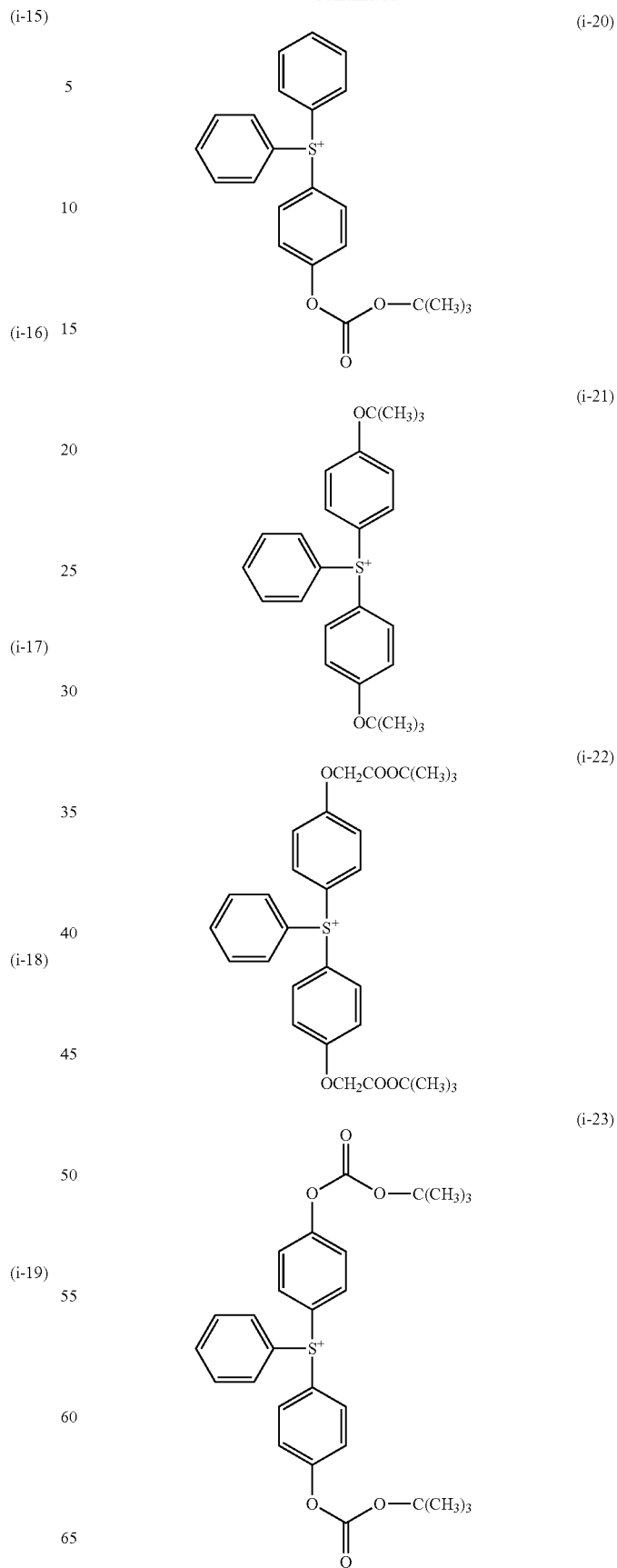

-continued
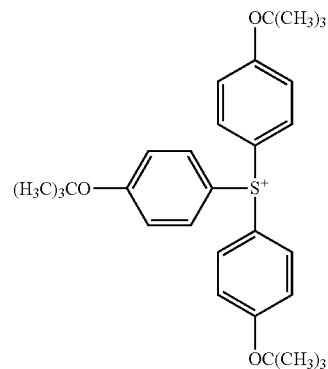
(i-24)
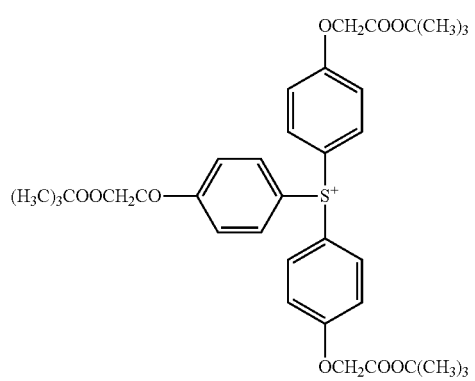
(i-25)
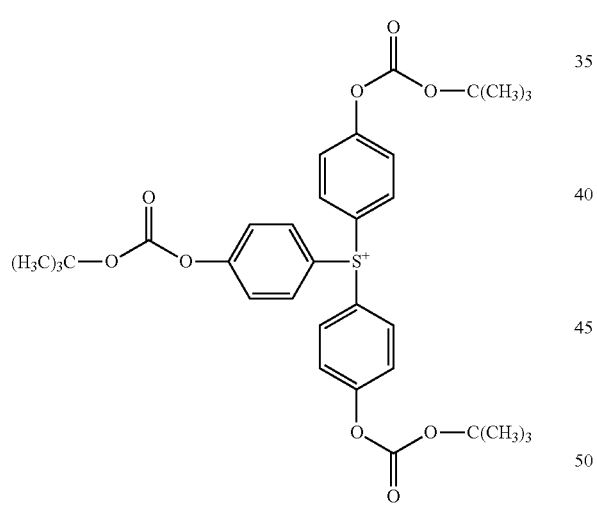
(i-26)
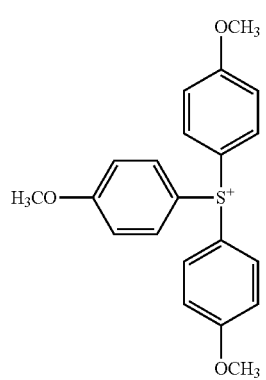
(i-27)
-continued
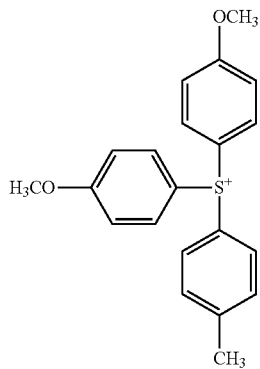
(i-28)
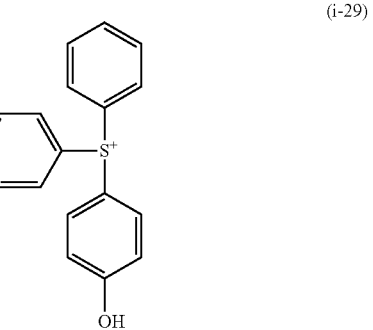
(i-29)
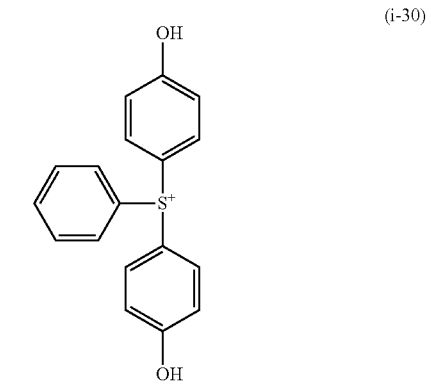
(i-30)
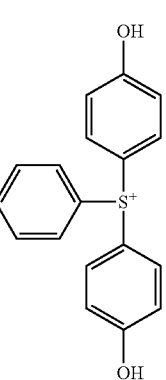
(i-31)

(i-32) 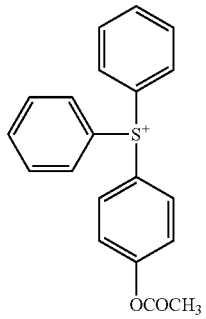
(i-33) 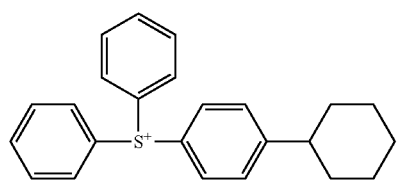
(i-34) 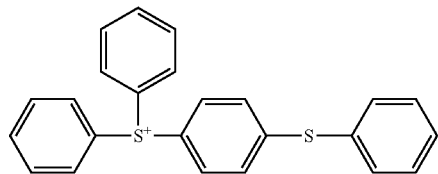
(i-35) 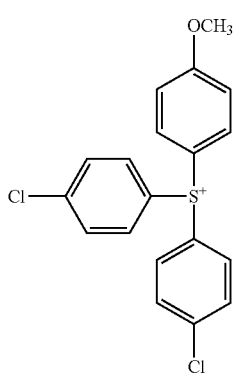
(i-36) 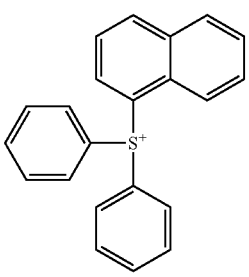
(i-37) 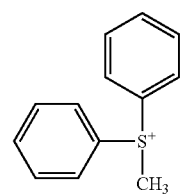
(i-38) 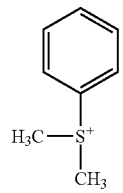
(i-39) 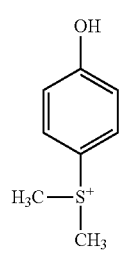
(i-40) 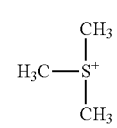
(i-41) 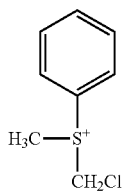
(i-42) 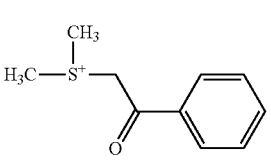
(i-43) 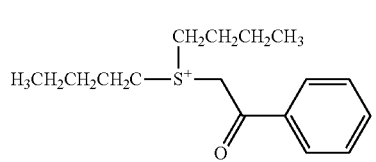
(i-44) 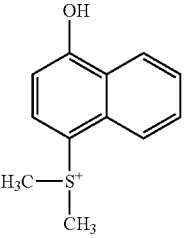
(i-45) 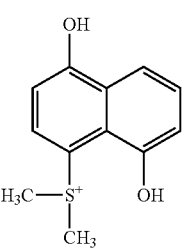

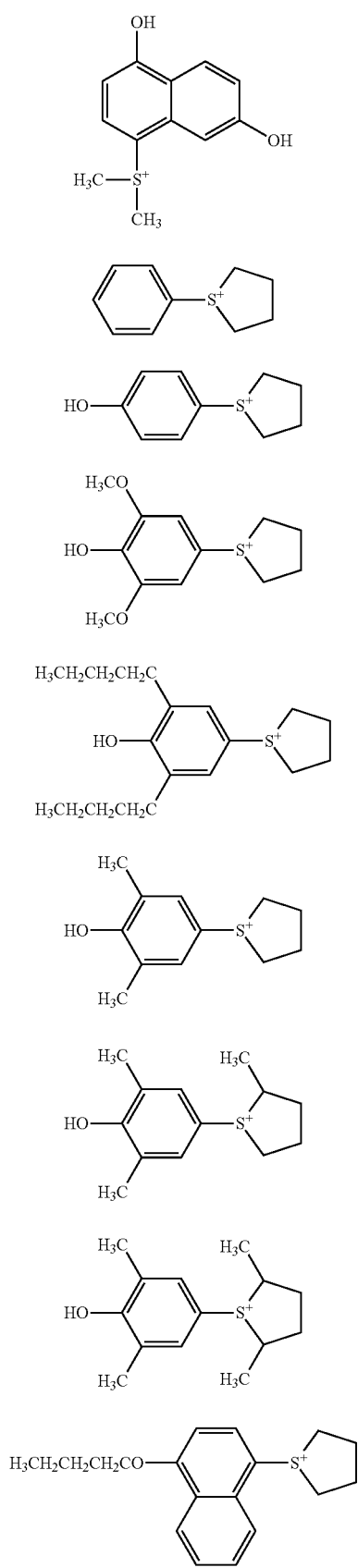
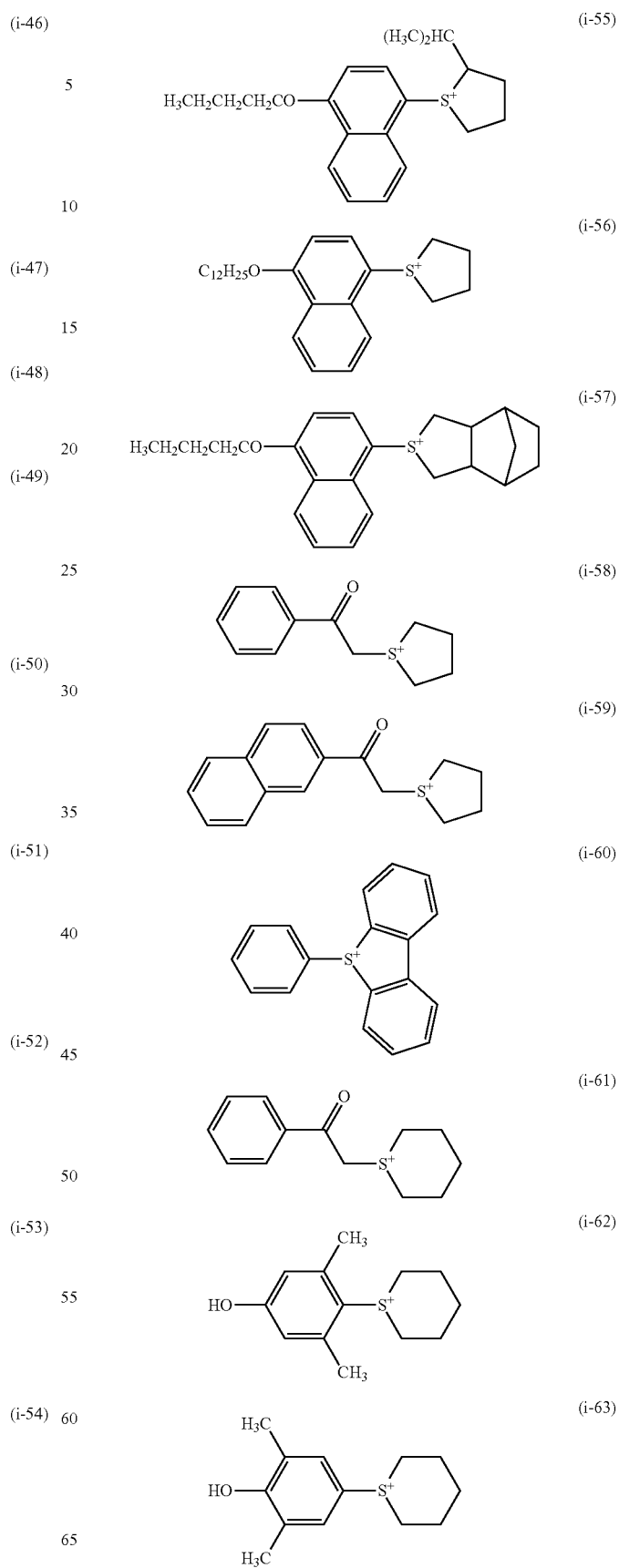

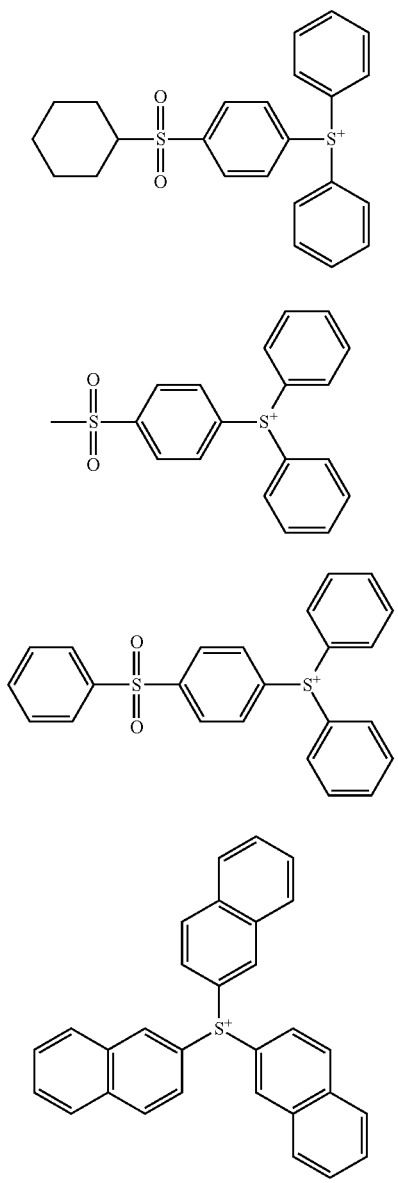
(i-64)
(i-65)
(i-66)
(i-67)
In addition, examples of the iodonium cation include cations represented by the following formulae (ii-1) to (ii-39), and the like.
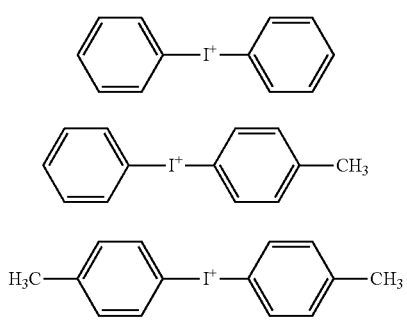
(ii-1)
(ii-2)
(ii-3)
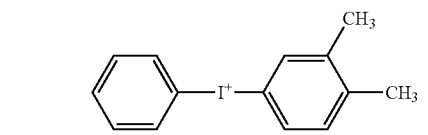
(ii-4)
(ii-5)
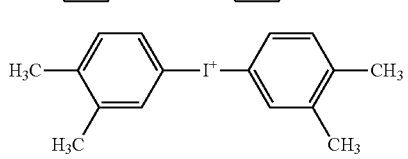
(ii-6)
(ii-7)
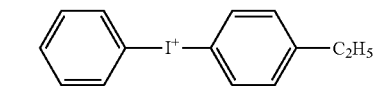
(ii-8)
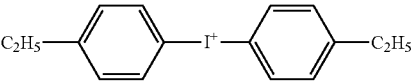
(ii-9)
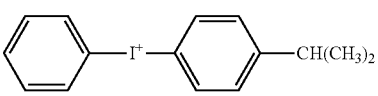
(ii-10)
(ii-11)
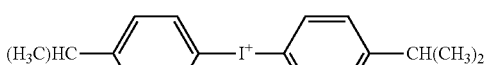
(ii-12)
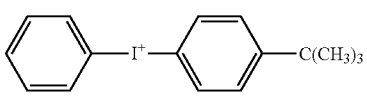
(ii-13)
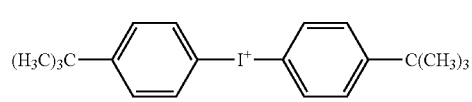
(ii-14)
(ii-15)
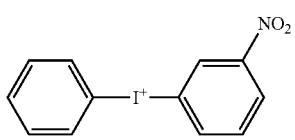
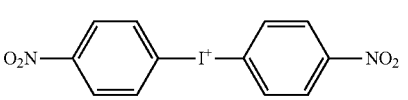
(ii-16)
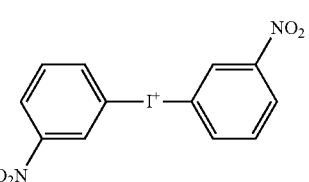
(ii-17)
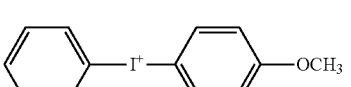
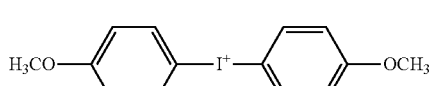

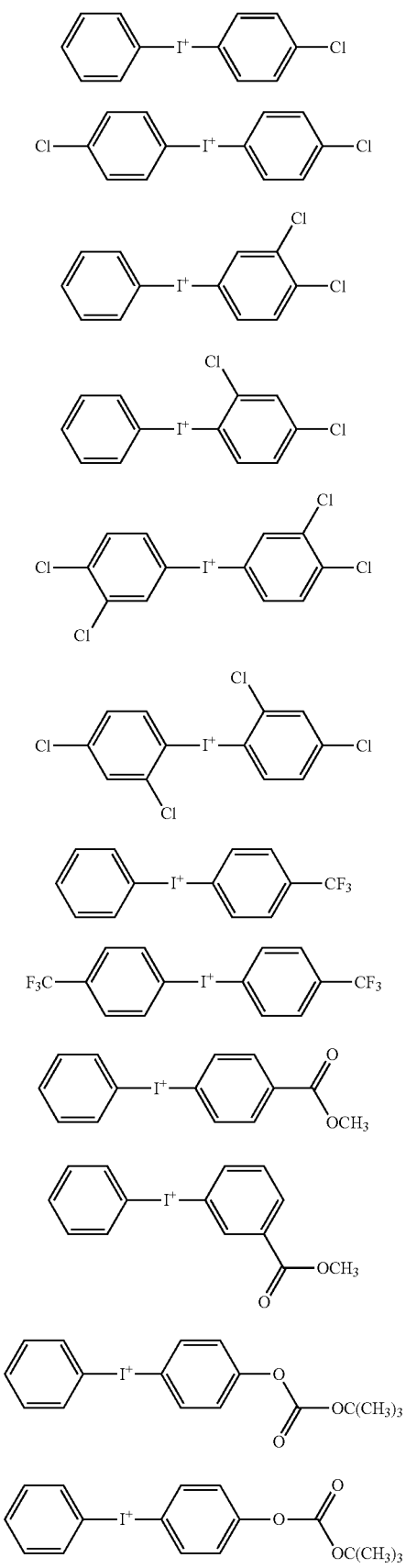
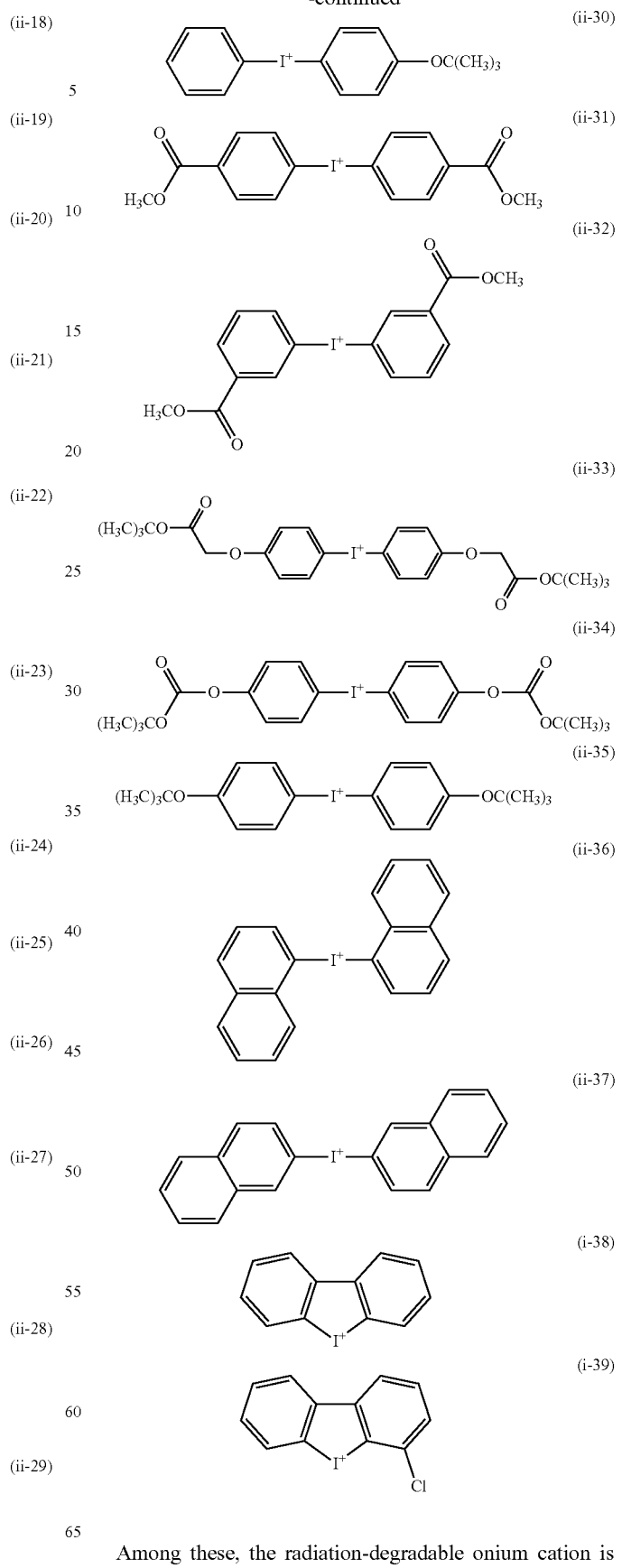
Among these, the radiation-degradable onium cation is preferably the sulfonium cation represented by (i-1) or the iodonium cation represented by (ii-1), and more preferably the sulfonium cation represented by (i-1).

Compound (I)

The compound (I) is not particularly limited as long as the sulfonate anion (A) and the radiation-degradable onium cation are included; however, the compound (I) is preferably a compound that includes a group represented by the following formula (1-1) or (1-2).

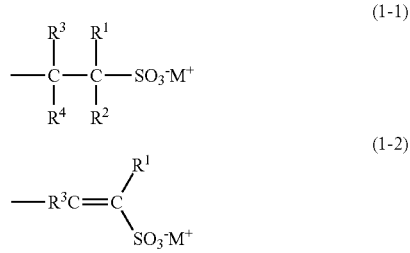

In the above formulae (1-1) and (1-2), $R^1$ and $R^2$ each independently represent a hydrogen atom or a monovalent electron-donating group; $R^3$ represents a monovalent electron-withdrawing group; $R^4$ represents a hydrogen atom or a monovalent hydrocarbon group, wherein two or more of $R^1$ to $R^4$ taken together may represent a ring structure together with the carbon atom to which they bond; and $M^+$ represents a monovalent radiation-degradable onium cation.

Examples of the monovalent electron-donating group which may be represented by $R^1$ or $R^2$ include the same groups as those exemplified hereinabove as the monovalent electron-donating group, and the like.

$R^1$ and $R^2$ represents preferably a hydrogen atom or a monovalent hydrocarbon group, more preferably a hydrogen atom or an alkyl group, still more preferably a hydrogen atom or a methyl group, and particularly preferably a hydrogen atom.

Examples of the monovalent electron-withdrawing group which may be represented by $R^3$ include the same groups as those exemplified hereinabove as the monovalent electron-withdrawing group, and the like. Among these, a cyano group, a fluorine atom and a monovalent fluorinated hydrocarbon group are preferred, a cyano group and a monovalent fluorinated hydrocarbon group are more preferred, a cyano group and a perfluoroalkyl group are still more preferred, and a cyano group and a trifluoromethyl group are particularly preferred.

Examples of the monovalent hydrocarbon group which may be represented by $R^4$ include monovalent linear hydrocarbon groups, monovalent alicyclic hydrocarbon groups, monovalent aromatic hydrocarbon groups, and the like.

$R^4$ represents preferably a hydrogen atom or a monovalent linear hydrocarbon group, more preferably a hydrogen atom or an alkyl group, and still more preferably a hydrogen atom in light of the ease in synthesis of the compound (I).

Examples of the ring structure which may be represented by the two or more of $R^1$ to $R^4$ taken together with the carbon atom to which they bond include:
  alicyclic structures such as a cyclobutane structure, a cyclopentane structure, a cyclohexane structure, a norbornane structure and an adamantane structure;
  aromatic ring structures such as a benzene structure, a toluene structure, a naphthalene structure and an anthracene structure; and the like.

Among these, ring structures which may be represented by $R^1$ and $R^3$ taken together are preferred, aromatic ring structures are more preferred, and a benzene structure is still more preferred.

The compound (I) may be, for example, in the form of a low molecular weight compound (hereinafter, may be also referred to as "acid generating agent (B)", as appropriately) or in the form of a polymer, or in both of these forms.

Examples of the compound (I) that is in the form of a low molecular weight compound include a compound represented by the following formula (2) (hereinafter, may be also referred to as "compound (I-1)"), and the like.

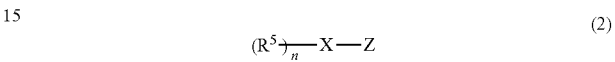

In the above formula (2), Z represents a group represented by the above formula (1-1) or (1-2); X represents a linking group having a valency of (n+1); n is an integer of 1 to 3, wherein in a case where n is 1, X may represent a single bond; $R^5$ represents a hydrogen atom or a monovalent organic group, wherein in a case where n is no less than 2, a plurality of $R^5$s may be identical or different; and two or more of Z, X and $R^5$ taken together may represent a ring structure.

Examples of the linking group having a valency of (n+1) which may be represented by X include:
  divalent linking groups (when n is 1) such as divalent hydrocarbon groups, —O—, —CO—, —COO—, —NR—, —CONH—, —S—, —$SO_2$—, —$SO_3$—, and groups obtained by combining two or more of these groups, and the like;
  trivalent linking groups (when n is 2) such as trivalent hydrocarbon groups, groups obtained by combining a trivalent hydrocarbon group with —O—, —CO—, —COO—, —NR—, —CONH—, —S—, —$SO_2$- or —$SO_3$—, and the like; and
  tetravalent linking groups (when n is 3) such as tetravalent hydrocarbon groups, groups obtained by combining a tetravalent hydrocarbon group with —O—, —CO—, —COO—, —NR—, —CONH—, —S—, —$SO_2$— or —$SO_3$—, and the like.

R in —NR— represents a monovalent hydrocarbon group.

In the above formula (2), n is preferably 1 or 2, and more preferably 1.

In a case where n is 1, X represents preferably a single bond, a divalent hydrocarbon group, —O—, —COO—, —NR—, —CONH—, —S—, —$SO_2$— or —$SO_3$—, and more preferably a single bond or —COO—.

Examples of the monovalent organic group which may be represented by $R^5$ include: monovalent hydrocarbon groups; hetero atom-containing groups that include, between adjacent carbon atoms of a hydrocarbon chain thereof, a group having a hetero atom; groups obtained by substituting a part or all of hydrogen atoms included in the hetero atom-containing groups with a substituent; and the like.

Examples of the monovalent hydrocarbon group include linear hydrocarbon groups having 1 to 20 carbon atoms, alicyclic hydrocarbon groups having 3 to 20 carbon atoms, aromatic hydrocarbon groups having 6 to 20 carbon atoms, and the like.

Examples of the linear hydrocarbon group include:
  alkyl groups such as a methyl group, an ethyl group, a propyl group and a butyl group;

alkenyl groups such as an ethenyl group, a propenyl group and a butenyl group;

alkynyl groups such as an ethynyl group, a propynyl group and a butynyl group; and the like.

Examples of the alicyclic hydrocarbon group include:

monocyclic cycloalkyl groups such as a cyclopropyl group, a cyclobutyl group, a cyclopentyl group and a cyclohexyl group;

polycyclic cycloalkyl groups such as a norbornyl group, an adamantyl group and a tricyclodecyl group;

monocyclic cycloalkenyl groups such as a cyclopropenyl group, a cyclobutenyl group, a cyclopentenyl group and a cyclohexenyl group;

polycyclic cycloalkenyl groups such as a norbornenyl group and a tricyclodecenyl group; and the like.

Examples of the aromatic hydrocarbon group include:

aryl groups such as a phenyl group, a tolyl group, a xylyl group, a naphthyl group and an anthryl group;

aralkyl groups such as a benzyl group, a phenethyl group and a naphthylmethyl group; and the like.

Examples of the group having a hetero atom include —O—, —CO—, —NH—, —S—, and combinations thereof.

Examples of the substituent include a hydroxy group, a carboxy group, oxyhydrocarbon groups, carbonyloxy hydrocarbon groups, an acyl group, an acyloxy group, a cyano group, a nitro group, a keto group (=O), and the like.

The organic group may be an acid-labile group. When the organic group is an acid-labile group, a carboxy group may be generated in the compound (I) existing at light-exposed sites, resulting in an improvement of the contrast between light-exposed sites and light-unexposed sites and the LWR performance of the radiation-sensitive resin composition. Examples of the acid-labile group include the same groups as those exemplified as the acid-labile group in the aforementioned polymer (A), and the like. Among these, hydrocarbon groups having a tertiary carbon atom to which X bonds are preferred, cycloalkyl groups having a tertiary carbon atom to which X bonds and an alkyl substituent on the tertiary carbon atom are more preferred, and 2-alkyl-2-adamantyl group is still more preferred.

$R^5$ represents preferably a monovalent organic group, more preferably a hydrocarbon group or a group that includes a lactone structure, still more preferably an alkyl group, a cycloalkyl group and a group that includes a lactone structure, and particularly preferably an ethyl group, a cyclohexyl group, an adamantyl group, a 2-methyl-2-adamantyl group, a 2-oxa-3-oxo-4,7,7-trimethylbicyclo[2.2.1]heptan-1-yl group and a norbornanelacton-2-yl group.

Examples of the ring structure which may be represented by the two or more of Z, X and $R^5$ taken together include the same ring structures as those that may be represented by $R^1$ to $R^4$ in the above formulae (1-1) and (1-2), and the like.

Examples of the compound (I-1) include compounds represented by the following formulae (2-1) to (2-13) (hereinafter, may be also referred to as "compounds (2-1) to (2-13)"), and the like.

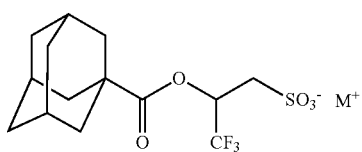
(2-1)

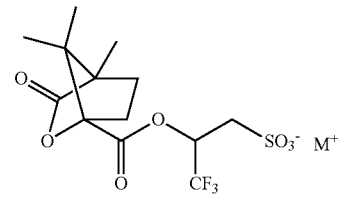
(2-2)

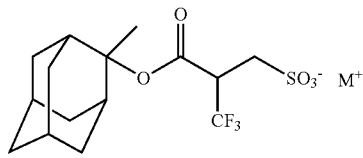
(2-3)

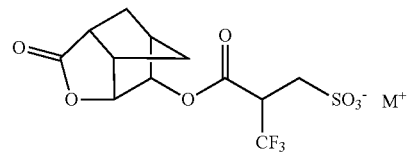
(2-4)

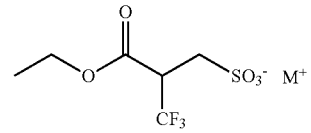
(2-5)

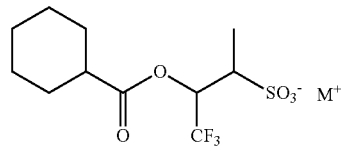
(2-6)

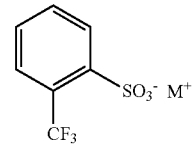
(2-7)

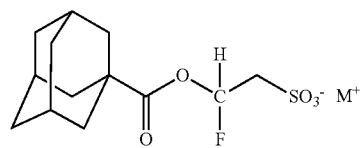
(2-8)

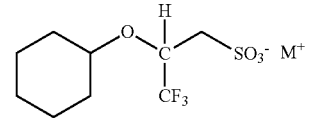
(2-9)

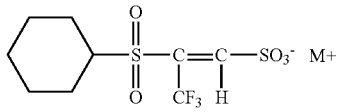
(2-10)

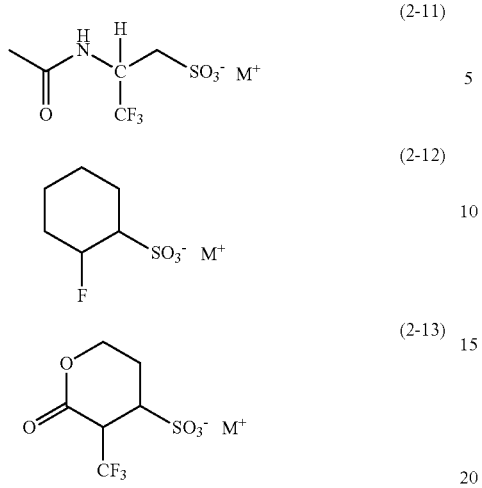

(2-11)

(2-12)

(2-13)

In the above formulae (2-1) to (2-13), $M^+$ represents a monovalent radiation-degradable onium cation.

Among these, the compounds (2-1) to (2-7) are preferred.

Examples of the compound (I) that is in the form of a polymer include polymers that have a structural unit represented by the following formula (3) (hereinafter, may be also referred to as "structural unit (a)"), and the like. The structural unit (a) may be incorporated into the aforementioned polymer (A).

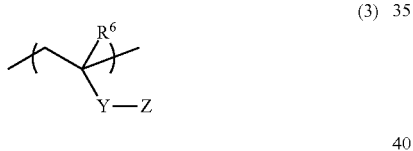

(3)

In the above formula (3), Z represents a group represented by the above formula (1-1) or (1-2); Y represents a divalent linking group; $R^6$ represents a hydrogen atom, a fluorine atom, a methyl group or a trifluoromethyl group; and Z and Y taken together may represent a ring structure.

Examples of the divalent linking group which may be represented by Y include groups exemplified as the divalent linking group among the linking group which may be represented by X in the above formula (2), and the like.

Among these, a single bond, divalent hydrocarbon groups, —O—, —COO—, and divalent groups obtained by combining the same are preferred.

$R^6$ represents preferably a hydrogen atom or a methyl group, and more preferably a methyl group in light of the copolymerizability of a monomer that gives the structural unit (a).

Examples of the ring structure which may be represented by Z and Y taken together include the same ring structures as those that may be represented by $R^1$ to $R^4$ in the above formulae (1-1) and (1-2), and the like.

Examples of the structural unit (a) include structural units represented by the following formulae (3-1) to (3-8) (hereinafter, may be also referred to as "structural units (3-1) to (3-8)"), and the like.

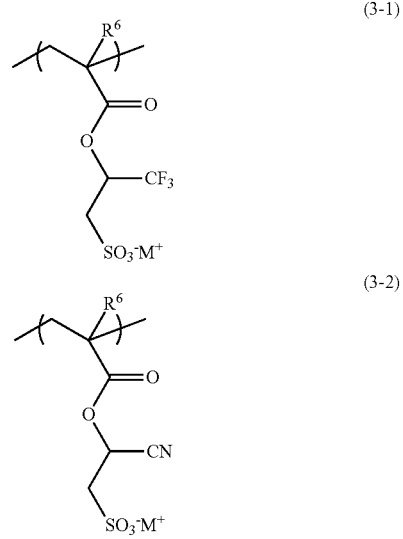

(3-1)

(3-2)

(3-3)

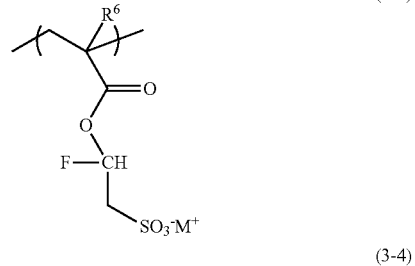

(3-4)

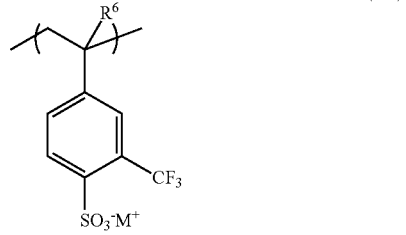

(3-5)

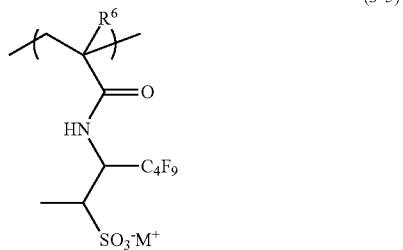

(3-6)

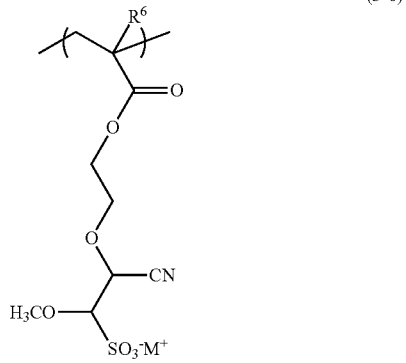

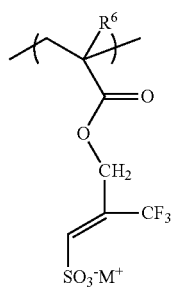

(3-7)

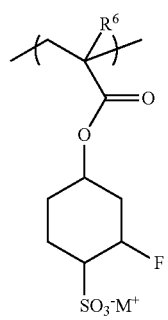

(3-8)

In the above formulae (3-1) to (3-8), $M^+$ represents a monovalent radiation-degradable onium cation.

Among these, the structural units (3-1) to (3-4) are preferred.

Method for Synthesis of Compound (I)

Regarding the synthesis of the compound (I), for example, in the case of a compound (I-1) wherein n in the above formula (2) is 1 and X represents —COO— (a carbonyl group being bound to $R^5$) (hereinafter, may be also referred to as "compound (2')"), the compound (I-1) can be synthesized according to the following scheme.

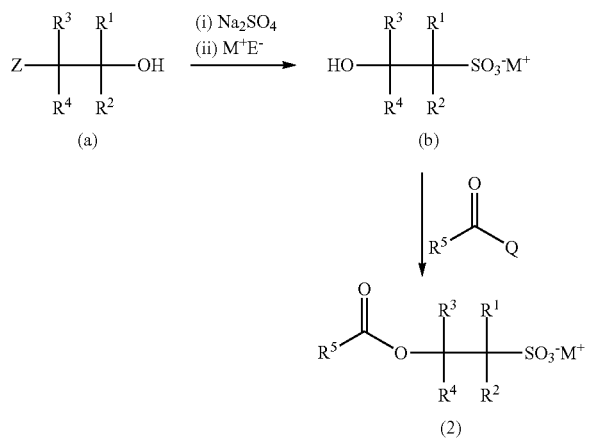

In the above scheme, $R^1$ and $R^2$ each independently represent a hydrogen atom or a monovalent electron-donating group; $R^3$ represents a monovalent electron-withdrawing group; $R^4$ represents a hydrogen atom or a monovalent hydrocarbon group, wherein two or more of $R^1$ to $R^4$ taken together may represent a ring structure together with the carbon atom to which they bond; Z represents a halogen atom; $M^+$ represents a monovalent radiation-degradable onium cation; $E^-$ represents a monovalent anion; $R^5$ represents a monovalent organic group; Q represents a halogen atom, —OH or —OCOR$^{11}$; and $R^{11}$ represents a monovalent hydrocarbon group.

Examples of the halogen atom which may be represented by Z and Q include a fluorine atom, a chlorine atom, a bromine atom, an iodine atom, and the like.

Among these, a chlorine atom and a bromine atom are preferred in light of an improvement of yields in synthesis reactions, and it is more preferred that Z represents a bromine atom and Q represents a chlorine atom.

A halogenated alcohol compound represented by the above formula (a) is reacted with sodium sulfate in a solvent such as water, and then is reacted with a salt that contains a radiation-degradable onium cation and is represented by the above formula $M^+E^-$ in a solvent such as dichloromethane/water to give a sulfonate salt that includes a hydroxy group and that may be represented by the above formula (b). The sulfonate salt is further reacted with a compound represented by the above formula $R^5COQ$ in a solvent such as dichloromethane in the presence of a base such as triethylamine or N,N'-dimethyl-4-aminopyridine to give a compound represented by the above formula (2').

Also, in the case of a compound (I-1) wherein n in the above formula (2) is 1 and X represents —COO— ($R^5$ being bound to —O—) (hereinafter, may be also referred to as "compound (2")"), the compound (I-1) can be synthesized according to the following scheme.

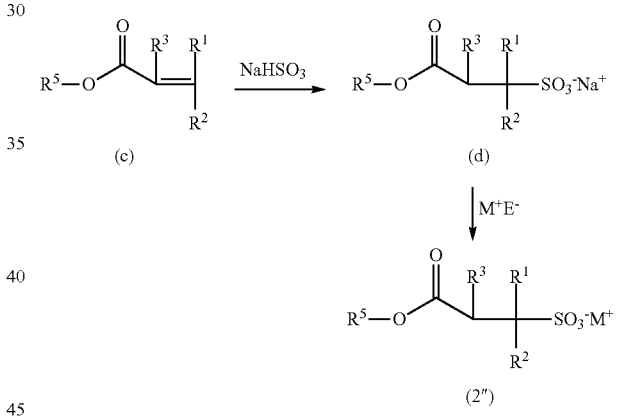

In the above scheme, $R^1$ and $R^2$ each independently represent a hydrogen atom or a monovalent electron-donating group; $R^3$ represents a monovalent electron-withdrawing group, wherein two or more of $R^1$ to $R^3$ as defined above taken together may represent an alicyclic structure together with the carbon atom to which they bond; $M^+$ represents a monovalent radiation-degradable onium cation; E represents a monovalent anion; and $R^5$ represents a monovalent organic group.

A compound represented by the above formula (c) is reacted with sodium bisulfite in a solvent such as a mixture of methanol, acetonitrile and water to form a sulfonic acid sodium salt represented by the above formula (d). Then, the sulfonic acid sodium salt is reacted with a salt that contains a radiation-degradable onium cation and is represented by the above formula $M^+E^-$ in a solvent such as dichloromethane to give a compound represented by the above formula (2").

Compounds (I) other than the compound (2') and the compound (2") can also be synthesized in a similar manner to the compound (2') and the compound (2").

Other Acid Generator

The acid generator (B) may contain an acid generator other than the compound (I) in addition to the compound (I) within a range not leading to impairment of the effects of the present invention. The other acid generator may be contained in the form of a low molecular weight compound (hereinafter, may be referred to as "other acid generating agent", as appropriately) or in the form of a polymer, or in both of these forms.

The other acid generating agent is not particularly limited as long as it is other than the compound (I), and examples thereof include onium salt compounds, N-sulfonyloxyimide compounds, and the like.

Examples of the onium salt compound include sulfonium salts, tetrahydrothiophenium salts, iodonium salts, phosphonium salts, diazonium salts, pyridinium salts, and the like.

Examples of the sulfonium salt include triphenylsulfonium trifluoromethanesulfonate, triphenylsulfonium nonafluoro-n-butanesulfonate, triphenylsulfonium perfluoro-n-octanesulfonate, triphenylsulfonium 2-bicyclo[2.2.1]hept-2-yl-1,1,2,2-tetrafluoroethanesulfonate, triphenylsulfonium 2-bicyclo[2.2.1]hept-2-yl-1,1-difluoroethanesulfonate, triphenylsulfonium camphorsulfonate, 4-cyclohexylphenyldiphenylsulfonium trifluoromethanesulfonate, 4-cyclohexylphenyldiphenylsulfonium nonafluoro-n-butanesulfonate, 4-cyclohexylphenyldiphenylsulfonium perfluoro-n-octanesulfonate, 4-cyclohexylphenyldiphenylsulfonium 2-bicyclo[2.2.1]hept-2-yl-1,1,2,2-tetrafluoroethanesulfonate, 4-cyclohexylphenyldiphenylsulfonium camphorsulfonate, 4-methanesulfonylphenyldiphenylsulfonium trifluoromethanesulfonate, 4-methanesulfonylphenyldiphenylsulfonium nonafluoro-n-butanesulfonate, 4-methanesulfonylphenyldiphenylsulfonium perfluoro-n-octanesulfonate, 4-methanesulfonylphenyldiphenylsulfonium 2-bicyclo[2.2.1]hept-2-yl-1,1,2,2-tetrafluoroethanesulfonate, 4-methanesulfonylphenyldiphenylsulfonium camphorsulfonate, triphenylsulfonium 1,1,2,2-tetrafluoro-6-(1-adamantanecarbonyloxy)hexane-1-sulfonate, triphenylsulfonium 1,1-difluoro-2-(adamantan-1-yl)ethane-1-sulfonate, and the like.

Examples of the tetrahydrothiophenium salt include 1-(4-n-butoxynaphthalen-1-yl)tetrahydrothiophenium trifluoromethanesulfonate, 1-(4-n-butoxynaphthalen-1-yl)tetrahydrothiophenium nonafluoro-n-butanesulfonate, 1-(4-n-butoxynaphthalen-1-yl)tetrahydrothiophenium perfluoro-n-octanesulfonate, 1-(4-n-butoxynaphthalen-1-yl)tetrahydrothiophenium 2-bicyclo[2.2.1]hept-2-yl-1,1,2,2-tetrafluoroethanesulfonate, 1-(4-n-butoxynaphthalen-1-yl)tetrahydrothiophenium camphorsulfonate, 1-(6-n-butoxynaphthalen-2-yl)tetrahydrothiophenium trifluoromethanesulfonate, 1-(6-n-butoxynaphthalen-2-yl)tetrahydrothiophenium nonafluoro-n-butanesulfonate, 1-(6-n-butoxynaphthalen-2-yl)tetrahydrothiophenium perfluoro-n-octanesulfonate, 1-(6-n-butoxynaphthalen-2-yl)tetrahydrothiophenium 2-bicyclo[2.2.1]hept-2-yl-1,1,2,2-tetrafluoroethanesulfonate, 1-(6-n-butoxynaphthalen-2-yl)tetrahydrothiophenium camphorsulfonate, 1-(3,5-dimethyl-4-hydroxyphenyl)tetrahydrothiophenium trifluoromethanesulfonate, 1-(3,5-dimethyl-4-hydroxyphenyl)tetrahydrothiophenium nonafluoro-n-butanesulfonate, 1-(3,5-dimethyl-4-hydroxyphenyl)tetrahydrothiophenium perfluoro-n-octanesulfonate, 1-(3,5-dimethyl-4-hydroxyphenyl)tetrahydrothiophenium 2-bicyclo[2.2.1]hept-2-yl-1,1,2,2-tetrafluoroethanesulfonate, 1-(3,5-dimethyl-4-hydroxyphenyl)tetrahydrothiophenium camphorsulfonate, and the like.

Examples of the iodonium salt include diphenyliodonium trifluoromethanesulfonate, diphenyliodonium nonafluoro-n-butanesulfonate, diphenyliodonium perfluoro-n-octanesulfonate, diphenyliodonium 2-bicyclo[2.2.1]hept-2-yl-1,1,2,2-tetrafluoroethanesulfonate, diphenyliodonium camphorsulfonate, bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, bis(4-t-butylphenyl)iodonium 2-bicyclo[2.2.1]hept-2-yl-1,1,2,2-tetrafluoroethanesulfonate, bis(4-t-butylphenyl)iodonium camphorsulfonate, and the like.

Examples of the N-sulfonyloxyimide compound include N-(trifluoromethanesulfonyloxy)bicyclo[2.2.1]hept-5-ene-2,3-dicarboxyimide, N-(nonafluoro-n-butanesulfonyloxy)bicyclo[2.2.1]hept-5-ene-2,3-dicarboxyimide, N-(perfluoro-n-octanesulfonyloxy)bicyclo[2.2.1]hept-5-ene-2,3-dicarboxyimide N-(2-bicyclo[2.2.1]hept-2-yl-1,1,2,2-tetrafluoroethane sulfonyloxy)bicyclo[2.2.1]hept-5-ene-2,3-dicarboxyimide, N-(2-(3-tetracyclo[4.4.0.1$^{2,5}$.1$^{7,10}$]dodecanyl)-1,1-difluoroethanesulfonyloxy)bicyclo[2.2.1]hept-5-ene-2,3-dicarboxyimide, N-(camphorsulfonyloxy)bicyclo[2.2.1]hept-5-ene-2,3-dicarboxyimide, and the like.

In the case of the acid generator (B) being the acid generating agent (B), the amount of the acid generator (B) with respect to 100 parts by mass of the polymer (A) falls within a range of preferably 0.1 parts by mass to 30 parts by mass, more preferably 0.5 parts by mass to 20 parts by mass, and still more preferably 1 part by mass to 15 parts by mass. When the amount of the acid generator (B) falls within the above range, the sensitivity of the radiation-sensitive resin composition can be improved, resulting in an improvement of the LWR performance.

In the case of the acid generator (B) being the acid generating agent (B), the percentage content of the compound (I) in the acid generator (B) falls within a range of preferably 20% by mass to 100% by mass, more preferably 25% by mass to 90% by mass, and still more preferably 30% by mass to 70% by mass. When the percentage content of the compound (I) falls within the above range, the LWR performance of the radiation-sensitive resin composition can be further improved.

In the case of the acid generator (B) being the acid generating agent (B), the amount of the compound (I) in the radiation-sensitive resin composition with respect to 100 parts by mass of the polymer (A) falls within a range of preferably 0.1 parts by mass to 30 parts by mass, more preferably 1 part by mass to 15 parts by mass, and still more preferably 2 parts by mass to 10 parts by mass. When the amount of the compound (I) falls within the above range, the LWR performance of the radiation-sensitive resin composition can be further improved.

(C) Acid Diffusion Controller

The radiation-sensitive resin composition according to the embodiment of the present invention may contain (C) an acid diffusion controller, as needed.

The acid diffusion controller (C) exerts the effect of controlling diffusion phenomenon of the acid generated from the acid generator (B) upon the exposure in the resist film, and inhibiting unfavorable chemical reactions in unexposed regions; as a result, storage stability of the resultant radiation-sensitive resin composition is further improved, and a resolution for use as a resist is further improved, while inhibiting variations of the line widths of the resist pattern caused by variations of post-exposure delay from the exposure until a development treatment, which enables the radiation-sensitive resin composition with superior process stability to be obtained. The acid diffusion controller (C) may be contained in the radiation-sensitive resin composition in the form of a low molecular weight compound (hereinafter, may be also referred to as "acid diffusion control agent (C)", as appropriately), in the form of a part of a polymer, or in both of these forms.

The acid diffusion control agent (C) is exemplified by a compound represented by the following formula (5a) (hereinafter, may be also referred to as "nitrogen atom-containing compound (I)"), a compound having two nitrogen atoms within a single molecule (hereinafter, may be also referred to as "nitrogen atom-containing compound (II)"), a compound having three nitrogen atoms within a single molecule (hereinafter, may be also referred to as "nitrogen atom-containing compound (III)"), an amide group-containing compound, a urea compound, a nitrogen atom-containing heterocyclic compound, and the like.

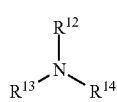

(5a)

In the above formula (5a), $R^{12}$, $R^{13}$ and $R^{14}$ each independently represent a hydrogen atom, an unsubstituted or substituted linear or branched alkyl group, an unsubstituted or substituted cycloalkyl group, an unsubstituted or substituted aryl group or an unsubstituted or substituted aralkyl group.

Examples of the nitrogen atom-containing compound (I) include: monoalkylamines such as n-hexylamine; dialkylamines such as di-n-butylamine; trialkylamines such as triethylamine; aromatic amines such as aniline; and the like.

Examples of the nitrogen atom-containing compound (II) include ethylenediamine, N,N,N',N'-tetramethylethylenediamine, and the like.

Examples of the nitrogen atom-containing compound (III) include: polyamine compound such as polyethyleneimine and polyallylamine; polymers of dimethylaminoethylacrylamide, etc.; and the like.

Examples of the amide group-containing compound include formamide, N-methylformamide, N,N-dimethylformamide, acetamide, N-methylacetamide, N,N-dimethylacetamide, propionamide, benzamide, pyrrolidone, N-methylpyrrolidone, and the like.

Examples of the urea compound include urea, methylurea, 1,1-dimethylurea, 1,3-dimethylurea, 1,1,3,3-tetramethylurea, 1,3-diphenylurea, tributylthiourea, and the like.

Examples of the nitrogen atom-containing heterocyclic compound include: pyridines such as pyridine and 2-methylpyridine; morpholines such as N-propylmorpholine and N-(undecylcarbonyloxyethyl)morpholine; imidazoles such as 2-phenylbenzimidazole; pyrazine; pyrazole; and the like.

A nitrogen atom-containing compound that includes an acid-labile group may also be used as the nitrogen atom-containing organic compound. Examples of the nitrogen atom-containing organic compound that includes an acid-labile group include N-t-butoxycarbonylpiperidine, N-t-butoxycarbonylimidazole, N-t-butoxycarbonylbenzimidazole, N-t-butoxycarbonyl-2-phenylbenzimidazole, N-(t-butoxycarbonyl)di-n-octylamine, N-(t-butoxycarbonyl)diethanolamine, N-(t-butoxycarbonyl)dicyclohexylamine, N-(t-butoxycarbonyl)diphenylamine, N-t-butoxycarbonyl-4-hydroxypiperidine, N-t-amyloxycarbonyl-4-hydroxypiperidine, and the like.

In addition, as the acid diffusion control agent (C), a photodegradable base which is sensitized upon exposure to generate a weak acid may be used. The photodegradable base is exemplified by an onium salt compound which is degraded upon the exposure and loses its acid diffusion controllability, and the like. Examples of the onium salt compound include sulfonium salt compounds represented by the following formula (5b-1), iodonium salt compounds represented by the following formula (5b-2), and the like.

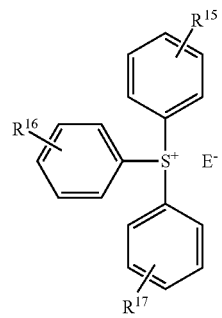

(5b-1)

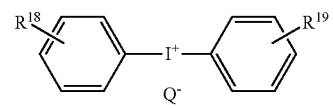

(5b-2)

In the above formulae (5b-1) and (5b-2), $R^{15}$ to $R^{19}$ each independently represent a hydrogen atom, an alkyl group, an alkoxy group, a hydroxy group or a halogen atom; $E^-$ and $Q^-$ each independently represent $OH^-$, $R^\beta$—$COO^-$, $R^\beta$—$SO_3^-$ or an anion represented by the following formula (5b-3), wherein $R^\beta$ represents an alkyl group, an aryl group or an aralkyl group.

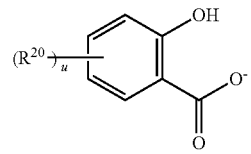

(5b-3)

In the above formula (5b-3), $R^{20}$ represents a linear or branched alkyl group having 1 to 12 carbon atoms or a linear or branched alkoxyl group having 1 to 12 carbon atoms, wherein a part or all of hydrogen atoms included in the linear or branched alkyl group or the linear or branched alkoxyl group may be substituted with a fluorine atom; and u is an integer of 0 to 2.

Examples of the photodegradable base include compounds represented by the following formulae, and the like.

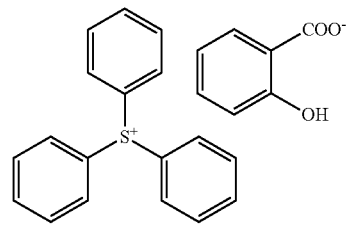

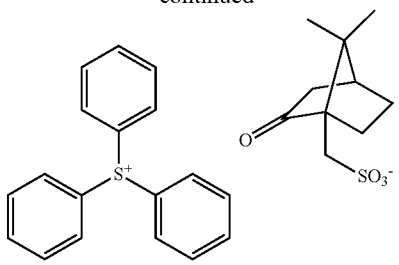

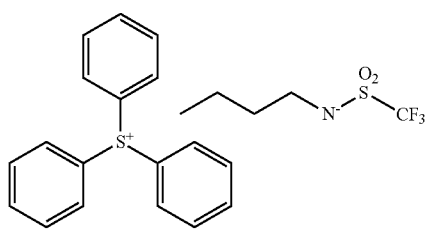

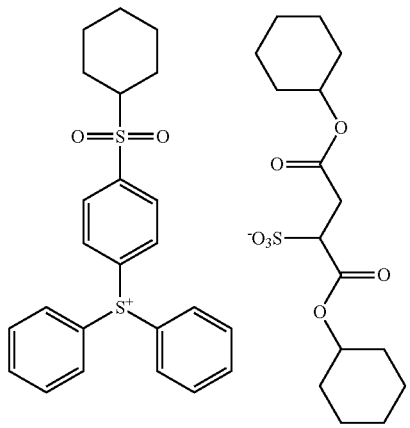

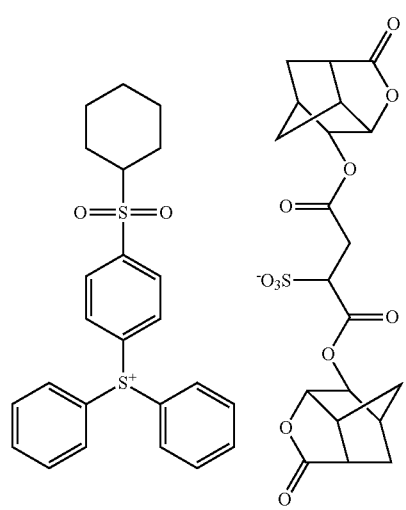

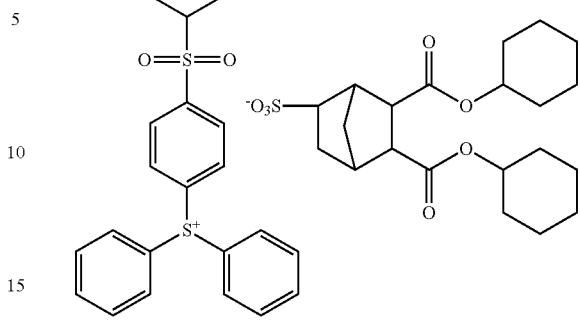

Among these, as the photodegradable base, sulfonium salts are preferred, triarylsulfonium salts are more preferred, and triphenylsulfonium salicylate and triphenylsulfonium 10-camphorsulfonate are still more preferred.

In the case of the acid diffusion controller (C) being the acid diffusion control agent (C), the amount of the acid diffusion controller (C) with respect to 100 parts by mass of the polymer (A) falls within a range of preferably 0 parts by mass to 20 parts by mass, more preferably 0.1 parts by mass to 15 parts by mass, and still more preferably 0.3 parts by mass to 10 parts by mass. When the amount of the acid diffusion control agent (C) is greater than the upper limit, the sensitivity of the radiation-sensitive resin composition may be deteriorated.

(D) Polymer

The polymer (D) is a fluorine atom-containing polymer (except for those falling under the polymer (A)). When the radiation-sensitive resin composition according to the embodiment of the present invention contains the polymer (D), in forming a resist film, the polymer (D) tends to be unevenly distributed in the vicinity of the surface of the resist film due to oil repellent characteristics of the fluorine-containing polymer in the film, and thus elution of the acid generating agent, the acid diffusion control agent and the like into a liquid immersion medium can be inhibited during an exposure through the liquid immersion medium. In addition, due to water repellent characteristics of the polymer (D), an advancing contact angle of a liquid immersion medium on a resist film can be controlled to fall within a desired range, whereby formation of bubble defects can be inhibited. Furthermore, a larger receding contact angle of a liquid immersion medium on a resist film is attained, thereby enabling an exposure by high-speed scanning without being accompanied by residual water beads. Thus, when the radiation-sensitive resin composition contains the polymer (D), a resist film suitable for a liquid immersion lithography process can be formed.

The polymer (D) is not particularly limited as long as the polymer (D) contains a fluorine atom; however, it is preferred that the polymer (D) has a higher percentage content (% by mass) of fluorine atoms than that of the polymer (A) in the radiation-sensitive resin composition. When the polymer (D) has a higher percentage content (% by mass) of fluorine atoms than that of the polymer (A), a higher degree of the aforementioned uneven distribution is attained, leading to an improvement of characteristics such as water repellency and elution inhibitory ability of the resultant resist film.

The percentage content of fluorine atoms of the polymer (D) falls within a range of preferably no less than 1% by mass, more preferably 2% by mass to 60% by mass, still more preferably 4% by mass to 40% by mass, and particularly preferably 7% by mass to 30% by mass. When the percentage content of fluorine atoms of the polymer (D) is less than the lower limit, the hydrophobicity of the surface of the resist film may be deteriorated. It is to be noted that the percentage content (% by mass) of fluorine atoms of a polymer can be calculated based on the structure of the polymer determined by $^{13}$C-NMR spectroscopy.

The polymer (D) preferably has the following structural unit (Da), the following structural unit (Db) or a combination thereof. The polymer (D) may have each one, or two or more types of the structural unit (Da) and/or the structural unit (Db).

Structural Unit (Da)

The structural unit (Da) is represented by the following formula (6a). When the polymer (D) has the structural unit (Da), the percentage content of fluorine atoms of the polymer (D) can be adjusted.

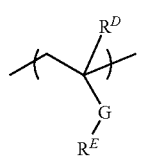

(6a)

In the above formula (6a), $R^D$ represents a hydrogen atom, a methyl group or a trifluoromethyl group; G represents a single bond, an oxygen atom, a sulfur atom, —CO—O—, —SO$_2$—O—NH—, —CO—NH— or —O—CO—NH—; $R^E$ represents a monovalent linear hydrocarbon group having 1 to 6 carbon atoms and at least one fluorine atom or a monovalent aliphatic cyclic hydrocarbon group having 4 to 20 carbon atoms and at least one fluorine atom.

Examples of the monovalent linear hydrocarbon group having 1 to 6 carbon atoms and at least one fluorine atom, which may be represented by $R^E$, include a trifluoromethyl group, a 2,2,2-trifluoroethyl group, a perfluoroethyl group, a 2,2,3,3,3-pentafluoropropyl group, a 1,1,1,3,3,3-hexafluoropropyl group, a perfluoro-n-propyl group, a perfluoro-i-propyl group, a perfluoro-n-butyl group, a perfluoro-i-butyl group, a perfluoro-t-butyl group, a 2,2,3,3,4,4,5,5-octafluoropentyl group, a perfluorohexyl group, and the like.

Examples of the monovalent aliphatic cyclic hydrocarbon group having 4 to 20 carbon atoms and at least one fluorine atom, which may be represented by $R^E$, include a monofluorocyclopentyl group, a difluorocyclopentyl group, a perfluorocyclopentyl group, a monofluorocyclohexyl group, a difluorocyclopentyl group, a perfluorocyclohexylmethyl group, a fluoronorbornyl group, a fluoroadamantyl group, a fluorobornyl group, a fluoroisobornyl group, a fluorotricyclodecyl group, a fluorotetracyclodecyl group, and the like.

Examples of a monomer that gives the structural unit (Da) include (meth)acrylic acid trifluoromethyl ester, (meth)acrylic acid 2,2,2-trifluoroethyl ester, (meth)acrylic acid 2,2,2-trifluoroethyloxycarbonylmethyl ester, (meth)acrylic acid perfluoroethyl ester, (meth)acrylic acid perfluoro-n-propyl ester, (meth)acrylic acid perfluoro-i-propyl ester, (meth)acrylic acid perfluoro-n-butyl ester, (meth)acrylic acid perfluoro-i-butyl ester, (meth)acrylic acid perfluoro-t-butyl ester, (meth)acrylic acid 2-(1,1,1,3,3,3-hexafluoropropyl) ester, (meth)acrylic acid 1-(2,2,3,3,4,4,5,5-octafluoropentyl) ester, (meth)acrylic acid perfluorocyclohexylmethyl ester, (meth)acrylic acid 1-(2,2,3,3,3-pentafluoropropyl) ester, (meth)acrylic acid monofluorocyclopentyl ester, (meth)acrylic acid difluorocyclopentyl ester, (meth)acrylic acid perfluorocyclopentyl ester, (meth)acrylic acid monofluorocyclohexyl ester, (meth)acrylic acid difluorocyclopentyl ester, (meth)acrylic acid perfluorocyclohexylmethyl ester, (meth)acrylic acid fluoronorbornyl ester, (meth)acrylic acid fluoroadamantyl ester, (meth)acrylic acid fluorobornyl ester, (meth)acrylic acid fluoroisobornyl ester, (meth)acrylic acid fluorotricyclodecyl ester, (meth)acrylic acid fluorotetracyclodecyl ester, and the like.

Among these, (meth)acrylic acid 2,2,2-trifluoroethyloxycarbonylmethyl ester is preferred.

The proportion of the structural unit (Da) with respect to the total structural units constituting the polymer (D) falls within a range of preferably 5 mol % to 95 mol %, more preferably 10 mol % to 90 mol %, and still more preferably 25 mol % to 80 mol %. When the proportion of the structural unit (Da) falls within the above range, a larger dynamic contact angle can be exhibited on the surface of the resist film in the exposure through a liquid immersion medium.

Structural Unit (Db)

The structural unit (Db) is represented by the following formula (6b). When the polymer (D) has the structural unit (Db), the hydrophobicity thereof may be enhanced, leading to a further increase of a dynamic contact angle on the surface of the resist film formed from the radiation-sensitive resin composition.

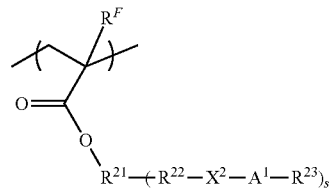

(6b)

In the above formula (6b), $R^F$ represents a hydrogen atom, a methyl group or a trifluoromethyl group; $R^{21}$ represents a hydrocarbon group having 1 to 20 carbon atoms and a valency of (s+1), which may further have an oxygen atom, a sulfur atom, —NR'—, a carbonyl group, —CO—O— or —CO—NH— bound at an end of $R^{21}$ on the $R^{22}$ side; R' represents a hydrogen atom or a monovalent organic group; $R^{22}$ represents a single bond, a divalent linear hydrocarbon group having 1 to 10 carbon atoms or a divalent aliphatic cyclic hydrocarbon group having 4 to 20 carbon atoms; $X^2$ represents a divalent linear hydrocarbon group having 1 to 20 carbon atoms and at least one fluorine atom; $A^1$ represents an oxygen atom, —NR"—, —CO—O—* or —SO$_2$—O—*, wherein R" represents a hydrogen atom or a monovalent organic group, and * denotes a binding site to $R^{21}$; $R^{23}$ represents a hydrogen atom or a monovalent organic group; s is an integer of 1 to 3, wherein in a case where s is 2 or 3, a plurality of $R^{22}$s may be identical or different, a plurality of $X^2$s may be identical or different, a plurality of $A^1$s may be identical or different, and a plurality of $R^{23}$s may be identical or different.

It is preferred that $R^{23}$ represents a hydrogen atom in light of the possibility of the improvement of the solubility of the polymer (D) in an alkaline developer solution.

Examples of the monovalent organic group which may be represented by $R^{23}$ include hydrocarbon groups having 1 to 30 carbon atoms and optionally including an acid-labile group, an alkali-labile group or a substituent, and the like.

Examples of the structural unit (Db) include structural units represented by the following formulae (6b-1) to (6b-3), and the like.

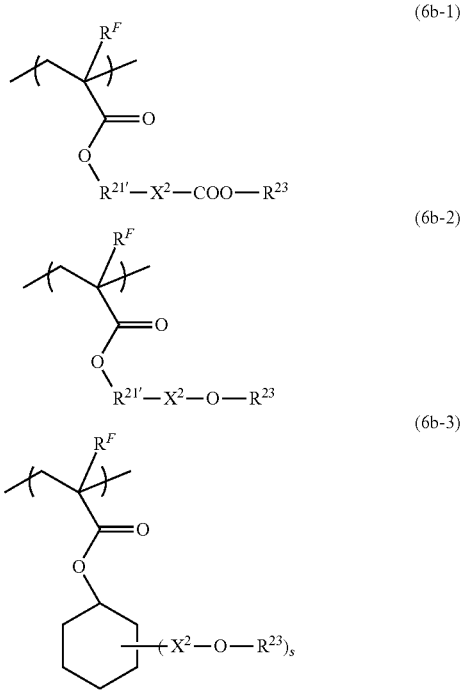

In the above formulae (6b-1) to (6b-3), $R^{2\prime\prime}$ represents a divalent linear, branched or cyclic saturated or unsaturated hydrocarbon group having 1 to 20 carbon atoms; $R^F$, $X^2$, $R^{23}$ and s are as defined in the above formula (6b), wherein in a case where s is 2 or 3, a plurality of $X^2$s may be identical or different, and a plurality of $R^{23}$s may be identical or different.

The proportion of the structural unit (6b) with respect to the total structural units constituting the polymer (D) falls within a range of preferably 0 mol % to 90 mol %, more preferably 5 mol % to 85 mol %, and still more preferably 10 mol % to 80 mol %. When the proportion of the structural unit (6b) falls within the above range, the degree of decrease of a dynamic contact angle on the surface of the resist film formed from the radiation-sensitive resin composition in a development with an alkali may be reduced.

Structural Unit (Dc)

The polymer (D) may have, in addition to the structural units (Da) and (Db), a structural unit that includes an acid-labile group (hereinafter, may be also referred to as "structural unit (Dc)") (except for those falling under the structural unit (Db)). When the polymer (D) has the structural unit (Dc), the configuration of the resultant resist pattern may be more favorable. Examples of the structural unit (Dc) include the structural unit (II) mentioned hereinabove in connection with the polymer (A), and the like.

The proportion of the structural unit (Dc) with respect to the total structural units constituting the polymer (D) falls within a range of preferably 5 mol % to 90 mol %, more preferably 10 mol % to 80 mol %, and still more preferably 15 mol % to 75 mol %. When the proportion of the structural unit (Dc) is less than the lower limit, formation of development defects in the resist pattern may be sufficiently inhibited. When the proportion of the structural unit (Dc) is greater than the upper limit, the hydrophobicity of the surface of the resultant resist film may be deteriorated.

Other Structural Unit

Also, the polymer (D) may have, in addition to the aforementioned structural units, other structural unit, for example: a structural unit that includes an alkali-soluble group; a structural unit that includes a structure of a lactone structure, a cyclic carbonate structure, a sultone structure or a combination thereof; a structural unit that includes an alicyclic group; and the like. Examples of the alkali-soluble group include a carboxy group, a sulfonamide group, a sulfo group, and the like. Examples of the structural unit that includes a structure of a lactone structure, a cyclic carbonate structure, a sultone structure or a combination thereof include the structural unit (III) mentioned hereinabove in connection with the polymer (A), and the like.

The proportion of the other structural unit with respect to the total structural units constituting the polymer (D) is typically no greater than 30 mol %, and preferably no greater than 20 mol %. When the proportion of the other structural unit is greater than the upper limit, the pattern formability of the radiation-sensitive resin composition may be deteriorated.

The amount of the polymer (D) in the radiation-sensitive resin composition with respect to 100 parts by mass of the polymer (A) falls within a range of preferably 0 to 20 parts by mass, more preferably 0.5 parts by mass to 15 parts by mass, and still more preferably 1 part by mass to 10 parts by mass. When the amount of the polymer (D) is greater than the upper limit, the pattern formability of the radiation-sensitive resin composition may be deteriorated.

(E) Solvent

The radiation-sensitive resin composition according to the embodiment of the present invention typically contains (E) a solvent. The solvent (E) is not particularly limited as long as it is capable of dissolving or dispersing at least the polymer (A) and the acid generator (B) as well as the acid diffusion controller (C) contained as desired, and the like.

Examples of the solvent (E) include alcohol solvents, ether solvents, ketone solvents, amide solvents, ester solvents, hydrocarbon solvents, and the like.

Examples of the alcohol solvent include:

monohydric alcohol solvents such as methanol, ethanol, n-propanol, iso-propanol, n-butanol, iso-butanol, sec-butanol, tert-butanol, n-pentanol, iso-pentanol, 2-methylbutanol, sec-pentanol, tert-pentanol, 3-methoxybutanol, n-hexanol, 2-methylpentanol, sec-hexanol, 2-ethylbutanol, sec-heptanol, 3-heptanol, n-octanol, 2-ethylhexanol, sec-octanol, n-nonyl alcohol, 2,6-dimethyl-4-heptanol, n-decanol, sec-undecyl alcohol, trimethylnonyl alcohol, sec-tetradecyl alcohol, sec-heptadecyl alcohol, furfuryl alcohol, phenol, cyclohexanol, methylcyclohexanol, 3,3,5-trimethylcyclohexanol, benzyl alcohol and diacetone alcohol;

polyhydric alcohol solvents such as ethylene glycol, 1,2-propylene glycol, 1,3-butylene glycol, 2,4-pentanediol, 2-methyl-2,4-pentanediol, 2,5-hexanediol, 2,4-heptanediol, 2-ethyl-1,3-hexanediol, diethylene glycol, dipropylene glycol, triethylene glycol and tripropylene glycol;

polyhydric alcohol partial ether solvents such as ethylene glycol monomethyl ether, ethylene glycol monoethyl ether, ethylene glycol monopropyl ether, ethylene glycol monobutyl ether, ethylene glycol monohexyl ether, ethylene glycol monophenyl ether, ethylene glycol mono-2-ethylbutyl ether, diethylene glycol monomethyl ether, diethylene glycol monoethyl ether, diethylene glycol monopropyl ether, diethylene glycol monobutyl ether, diethylene glycol monohexyl ether, propylene glycol monomethyl ether, propylene glycol monoethyl ether, propylene glycol monopropyl ether, propylene glycol monobutyl ether, dipropylene glycol monomethyl ether, dipropylene glycol monoethyl ether and dipropylene glycol monopropyl ether; and the like.

Examples of the ether solvent include:

dialkyl ether solvents such as diethyl ether, dipropyl ether and dibutyl ether;

cyclic ether solvents such as tetrahydrofuran and tetrahydropyran;

aromatic ring-containing ether solvents such as diphenyl ether and anisole (methyl phenyl ether); and the like.

Examples of the ketone solvent include:

linear ketone solvents such as acetone, butanone, methyl n-propyl ketone, methyl n-butyl ketone, diethyl ketone, methyl iso-butyl ketone, 2-heptanone (methyl n-pentyl ketone), ethyl n-butyl ketone, methyl n-hexyl ketone, di-iso-butyl ketone and trimethylnonanone;

cyclic ketone solvents such as cyclopentanone, cyclohexanone, cycloheptanone, cyclooctanone and methylcyclohexanone;

2,4-pentanedione, acetonyl acetone and acetophenone; and the like.

Examples of the amide solvent include:

cyclic amide solvents such as N,N'-dimethylimidazolidinone and N-methylpyrrolidone;

linear amide solvents such as N-methylformamide, N,N-dimethylformamide, N,N-diethylformamide, acetamide, N-methylacetamide, N,N-dimethylacetamide and N-methylpropionamide; and the like.

Examples of the ester solvent include:

acetic acid ester solvents such as methyl acetate, ethyl acetate, n-propyl acetate, iso-propyl acetate, n-butyl acetate, iso-butyl acetate, sec-butyl acetate, n-pentyl acetate, i-pentyl acetate, sec-pentyl acetate, 3-methoxybutyl acetate, methylpentyl acetate, 2-ethylbutyl acetate, 2-ethylhexyl acetate, benzyl acetate, cyclohexyl acetate, methylcyclohexyl acetate and n-nonyl acetate;

polyhydric alcohol partial ether acetate solvents such as ethylene glycol monomethyl ether acetate, ethylene glycol monoethyl ether acetate, diethylene glycol monomethyl ether acetate, diethylene glycol monoethyl ether acetate, diethylene glycol mono-n-butyl ether acetate, propylene glycol monomethyl ether acetate, propylene glycol monoethyl ether acetate, propylene glycol monopropyl ether acetate, propylene glycol monobutyl ether acetate, dipropylene glycol monomethyl ether acetate and dipropylene glycol monoethyl ether acetate;

lactone solvents such as γ-butyrolactone and valerolactone;

carbonate solvents such as diethyl carbonate, ethylene carbonate and propylene carbonate;

glycol diacetate, methoxytriglycol acetate, ethyl propionate, n-butyl propionate, iso-amyl propionate, diethyl oxalate, di-n-butyl oxalate, methyl acetoacetate, ethyl acetoacetate, methyl lactate, ethyl lactate, n-butyl lactate, n-amyl lactate, diethyl malonate, dimethyl phthalate and diethyl phthalate; and the like.

Examples of the hydrocarbon solvent include:

aliphatic hydrocarbon solvents such as n-pentane, iso-pentane, n-hexane, iso-hexane, n-heptane, iso-heptane, 2,2,4-trimethylpentane, n-octane, iso-octane, cyclohexane and methylcyclohexane;

aromatic hydrocarbon solvents such as benzene, toluene, xylene, mesitylene, ethylbenzene, trimethylbenzene, methylethylbenzene, n-propylbenzene, iso-propylbenzene, diethylbenzene, iso-butylbenzene, triethylbenzene, di-iso-propylbenzene and n-amylnaphthalene; and the like.

Among these, ester solvents and ketone solvents are preferred, polyhydric alcohol partial ether acetate solvents, cyclic ketone solvents and lactone solvents are more preferred, and propylene glycol monomethyl ether acetate, cyclohexanone and γ-butyrolactone are still more preferred. The radiation-sensitive resin composition may contain either one, or two or more types of the solvent (E).

Other Optional Component

The radiation-sensitive resin composition may contain other optional component in addition to the aforementioned components (A) to (E). Examples of the other optional component include a surfactant, a compound having an alicyclic skeleton, a sensitizing agent, and the like. These other optional components each may be used either alone of one type, or in combination of two or more types thereof.

Surfactant

The surfactant exerts the effect of improving coating property, striation, developability and the like of the radiation-sensitive resin composition. Examples of the surfactant include: nonionic surfactants such as polyoxyethylene lauryl ether, polyoxyethylene stearyl ether, polyoxyethylene oleyl ether, polyoxyethylene n-octyl phenyl ether, polyoxyethylene n-nonyl phenyl ether, polyethylene glycol dilaurate and polyethylene glycol distearate; commercially available product such as KP341 (manufactured by Shin-Etsu Chemical Co., Ltd.), Polyflow No. 75 and No. 95 (each manufactured by Kyoeisha Chemical Co., Ltd.), EFTOP EF301, EF303 and EF352 (each manufactured by Tochem Products Co. Ltd.), Megaface F171 and F173 (each manufactured by DIC), Fluorad FC430 and FC431 (each manufactured by Sumitomo 3M Limited), ASAHI GUARD AG710, Surflon S-382, SC-101, SC-102, SC-103, SC-104, SC-105 and SC-106 (each manufactured by Asahi Glass Co., Ltd.); and the like. The amount of the surfactant in the radiation-sensitive resin composition with respect to 100 parts by mass of the polymer (A) is typically no greater than 2 parts by mass.

Compound Having Alicyclic Skeleton

The compound having an alicyclic skeleton exerts the effect of improving dry etching resistance, a pattern configuration, adhesiveness to a substrate, and the like.

Examples of the compound having an alicyclic skeleton include:

adamantane derivatives such as 1-adamantanecarboxylic acid, 2-adamantanone and t-butyl 1-adamantanecarboxylate;

deoxycholic acid esters such as t-butyl deoxycholate, t-butoxycarbonylmethyl deoxycholate and 2-ethoxyethyl deoxycholate;

lithocholic acid esters such as t-butyl lithocholate, t-butoxycarbonylmethyl lithocholate and 2-ethoxyethyl lithocholate;

3-[2-hydroxy-2,2-bis(trifluoromethyl)ethyl]tetracyclo[4.4.0.1$^{2,5}$.1$^{7,10}$]dodecane and 2-hydroxy-9-methoxycarbonyl-5-oxo-4-oxa-tricyclo[4.2.1.0$^{3,7}$]nonane; and the like. The amount of the compound having an alicyclic skeleton in the radiation-sensitive resin composition with respect to 100 parts by mass of the polymer (A) is typically no greater than 5 parts by mass.

Sensitizing Agent

The sensitizing agent exhibits the action of increasing the amount of the acid produced from the acid generating agent (B) or the like, and exerts the effect of improving "apparent sensitivity" of the radiation-sensitive resin composition.

Examples of the sensitizing agent include carbazoles, acetophenones, benzophenones, naphthalenes, phenols, biacetyls, eosins, rose bengals, pyrenes, anthracenes, phenothiazines, and the like. These sensitizing agents may be used either alone, or two or more types thereof may be used in combination. The amount of the sensitizing agent in the radiation-sensitive resin composition with respect to 100 parts by mass of the polymer (A) is typically no greater than 2 parts by mass.

Method for Preparation of Radiation-Sensitive Resin Composition

The radiation-sensitive resin composition may be prepared, for example, by mixing the polymer (A) and the acid generator (B) as well as the acid diffusion control agent (C), the polymer (D), etc. as needed with the solvent (E) in a predetermined ratio. After the mixing, the radiation-sensitive resin composition is preferably filtered through a filter with a pore size of about 0.05 μm, for example. The solid content concentration of the radiation-sensitive resin composition falls within a range of typically 0.1% by mass to 50% by mass, preferably 0.5% by mass to 30% by mass, and more preferably 1% by mass to 20% by mass.

Resist Pattern-Forming Method

A resist pattern-forming method according to another embodiment of the present invention includes:

providing a resist film using the radiation-sensitive resin composition (hereinafter, may be also referred to as "resist film-providing step");

exposing the resist film (hereinafter, may be also referred to as "exposure step"); and developing the exposed resist film (hereinafter, may be also referred to as "development step").

According to the resist pattern-forming method, a resist pattern with reduced LWR can be formed as a result of the use of the aforementioned radiation-sensitive resin composition. Hereinafter, each step will be explained.

Resist Film-Providing Step

In this step, a resist film is provided using the radiation-sensitive resin composition according to the embodiment of the present invention. Examples of a substrate on which the resist film is provided include conventionally well-known substrates such as a silicon wafer and a wafer coated with silicon dioxide or aluminum. In addition, an organic or inorganic antireflective film disclosed in, for example, Japanese Examined Patent Application, Publication No. H6-12452, Japanese Unexamined Patent Application, Publication No. S59-93448, or the like may be provided on the substrate. A method for coating the radiation-sensitive resin composition is exemplified by spin-coat (spin-coating), cast coating, roll coating, and the like. After coating the radiation-sensitive resin composition, prebaking (PB) may be executed as needed for allowing a solvent in the coating film to be volatilized. The temperature for PB falls within a range of typically 60° C. to 140° C., and preferably 80° C. to 120° C. The time for PB falls within a range of typically 5 sec to 600 sec, and preferably 10 sec to 300 sec. The film thickness of the resist film provided falls within a range of 10 nm to 1,000 nm, and more preferably 10 nm to 500 nm.

In a case where an exposure through a liquid immersion medium is carried out and the radiation-sensitive resin composition does not contain a water repellent polymer additive such as the aforementioned polymer (D), etc., a liquid immersion liquid-insoluble protective film for liquid immersion may be provided on the resultant resist film for the purpose of avoiding a direct contact of the resist film with a liquid immersion liquid. As the protective film for liquid immersion, any one of a solvent-peelable protective film that is peeled by a solvent before the development step (see, for example, Japanese Unexamined Patent Application, Publication No. 2006-227632) and a developer solution-peelable protective film that is peeled concomitantly with the development in the development step (see, for example, WO 2005/069076 and WO 2006/035790) may be used. However, a developer solution-peelable protective film for liquid immersion is preferably used in light of throughput.

Exposure Step

In this step, the resist film provided in the resist film-providing step is exposed by irradiating with a radiation through a photomask (through a liquid immersion medium such as water, as needed). Examples of the radiation for use in the exposure include: electromagnetic radiations such as visible light rays, ultraviolet rays, far ultraviolet rays, X-rays and γ rays; charged particle rays such as electron beams and α rays; and the like, in accordance with the line width of the intended pattern. Among these, far ultraviolet rays and electron beams are preferred, an ArF excimer laser beam (wavelength: 193 nm), a KrF excimer laser beam (wavelength: 248 nm) and electron beams are more preferred, and an ArF excimer laser beam and electron beams are still more preferred.

In a case where the exposure is executed through a liquid immersion medium, examples of the liquid immersion liquid for use in the exposure include water, fluorine-containing inert liquids, and the like. It is preferred that the liquid immersion liquid is transparent to the exposure wavelength, and has a temperature coefficient of the refractive index as small as possible so that distortion of an optical image projected onto the film is minimized. In particular, when an ArF excimer laser beam (wavelength 193 nm) is used as an exposure light source, it is preferred to use water in light of availability and ease of handling thereof in addition to the aforementioned considerations. When water is used, a slight amount of an additive which reduces the surface tension of water and imparts enhanced surfactant power may be added. It is preferred that the additive hardly dissolves a resist film on a wafer and has a negligible influence on an optical coating of an inferior face of a lens. The water for use is preferably distilled water.

It is preferred that post exposure baking (PEB) is carried out after the exposure to facilitate dissociation of the acid-labile group included in the polymer (A), etc. mediated by the acid generated from the acid generator (B) at exposed sites of the resist film upon the exposure. This PEB makes the difference between the solubilities of the resist film in a developer solution at light-exposed sites and at light-unexposed sites. The temperature for PEB falls within a range of typically 50° C. to 180° C., and preferably 80° C. to 130° C. The time for PEB falls within a range of typically 5 sec to 600 sec, and preferably 10 sec to 300 sec.

Development Step

In this step, the resist film exposed in the exposure step is developed. This permits a predetermined resist pattern to be formed. After the development, washing with a rinse agent such as water or an alcohol and drying is typically carried out.

Examples of the developer solution for use in the development, in particular a development with an alkali, include alkali aqueous solutions that contain at least one type of alkaline compounds such as sodium hydroxide, potassium hydroxide, sodium carbonate, sodium silicate, sodium metasilicate, aqueous ammonia, ethylamine, n-propylamine, diethylamine, di-n-propylamine, triethylamine, methyldiethylamine, ethyldimethylamine, triethanolamine, tetramethylammonium hydroxide (TMAH), pyrrole, piperidine, choline, 1,8-diazabicyclo-[5.4.0]-7-undecene and 1,5-diazabicyclo-[4.3.0]-5-nonene in a dissolved form; and the like. Among these, an aqueous TMAH solution is preferred, and a 2.38% by mass aqueous TMAH solution is more preferred.

Alternatively, in the case of a development with an organic solvent, examples of the developer solution for use in the development include organic solvents such as hydrocarbon solvents, ether solvents, ester solvents, ketone solvents and alcohol solvents, or solvents containing an organic solvent. Examples of the organic solvent include either one, or two or more of solvents enumerated as examples of the aforementioned solvent (E) in the radiation-sensitive resin composition, and the like. Among these, ester solvents and ketone solvents are preferred. As the ester solvent, acetic acid ester solvents are preferred, and n-butyl acetate is more preferred. As the ketone solvent, linear ketones are preferred, and 2-heptanone is more preferred. The percentage content of the organic solvent in the developer solution is preferably no less than 80% by mass, more preferably no less than 90% by mass, still more preferably no less than 95% by mass, and particularly preferably no less than 99% by mass. Examples of a component other than the organic solvent in the developer solution include water, silicone oil, and the like.

Examples of the development method include: a dipping method in which the substrate is immersed for a given time period in a container filled with the developer solution; a puddle method in which the developer solution is placed to form a dome-shaped bead by way of the surface tension on the surface of the substrate for a given time period to conduct a development; a spraying method in which the developer solution is sprayed onto the surface of the substrate; a dynamic dispensing method in which the developer solution is continuously applied onto the substrate that is rotated at a constant speed while scanning with a developer solution application nozzle at a constant speed; and the like.

Acid Generator

An acid generator according to still another embodiment of the present invention includes a compound that includes:
 a sulfonate anion having $SO_3^-$, wherein a hydrogen atom or an electron-donating group bonds to an α carbon atom with respect to $SO_3^-$, and an electron-withdrawing group bonds to a β carbon atom with respect to $SO_3^-$; and
 a radiation-degradable onium cation.

The acid generator enables the LWR performance of a radiation-sensitive resin composition containing the same to be improved. Therefore, the acid generator can be suitably used as a component of the radiation-sensitive resin composition.

Compound

A compound according to yet still another embodiment of the present invention includes:
 sulfonate anion having $SO_3^-$, wherein a hydrogen atom or an electron-donating group bonds to an α carbon atom with respect to $SO_3^-$, and an electron-withdrawing group bonds to a β carbon atom with respect to $SO_3^-$; and
 a radiation-degradable onium cation.

The compound can be suitably used as the acid generator since the compound exhibits the aforementioned properties.

The acid generator and the compound have been explained hereinabove in the section of the acid generator (B) of the radiation-sensitive resin composition.

EXAMPLES

Hereinafter, the present invention will be described in detail by way of Examples, but the present invention should not be construed as being limited by the Examples. Methods for measuring various types of physical properties are shown below.

Mw and Mn

The Mw and Mn of a polymer were determined by gel permeation chromatography using GPC columns (G2000HXL×2, G3000HXL×1, G4000HXL×1, manufactured by Tosoh Corporation) under the following conditions:
 column temperature: 40° C.
 elution solvent: tetrahydrofuran (manufactured by Wako Pure Chemical Industries, Ltd.)
 flow rate: 1.0 mL/min
 sample concentration: 1.0% by mass
 amount of injected sample: 100 μL
 detector: differential refractometer
 standard substance: mono-dispersed polystyrene $^1$H-NMR and $^{13}$C-NMR Analyses $^1$H-NMR and $^{13}$C-NMR analyses were conducted using a nuclear magnetic resonance apparatus (JNM-EX270, manufactured by JEOL, Ltd.).

Synthesis of Compound

Example 1

Synthesis of Compound (B1-1)

A compound represented by the following formula (B1-1) was synthesized according to the following scheme.

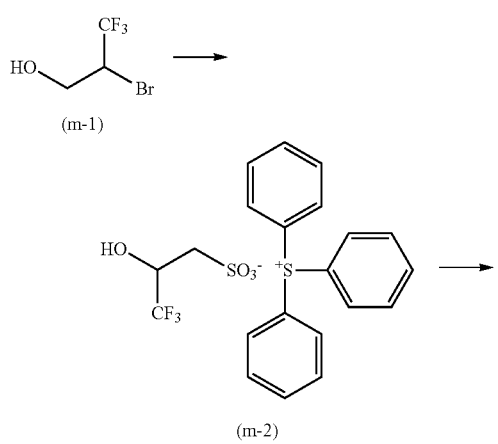

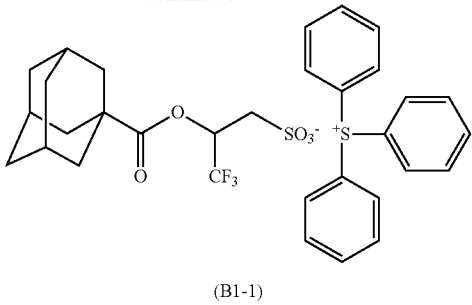

(B1-1)

Synthesis of Compound (m-2)

To a 200 mL eggplant shaped flask were charged 5.0 g (26 mmol) of 2-bromo-3,3,3-trifluoropropan-1-ol (the compound (m-1)), 6.5 g (52 mmol) of $Na_2SO_4$ and 40 mL of $H_2O$, and the mixture was stirred at 85° C. for 48 hours under a nitrogen atmosphere. After cooling to room temperature, 7.5 g (25 mmol) of triphenylsulfonium chloride and 120 mL of dichloromethane were added to the reaction solution, and the mixture was stirred at room temperature for 3 hours. After completing the reaction, only the organic layer was recovered, and the recovered organic layer was washed three times with 20 mL of water and dried over anhydrous magnesium sulfate. Thereafter, the residue obtained by concentrating the organic layer in vacuo was purified by silica gel column chromatography (developing solvent: dichloromethane/MeOH=10/1 (volume ratio)) to obtain 6.2 g of a compound (m-2) (yield 52%).

Synthesis of Compound (B1-1)

Into a 300 mL reaction flask were charged 5.0 g (11 mmol) of the compound (m-2) obtained above, 1.2 g (12 mmol) of triethylamine, 0.13 g (1.1 mmol) of N,N-dimethyl-4-aminopyridine and 100 mL of dichloromethane. The dichloromethane solution was cooled to 0° C., and to this was slowly added dropwise a solution prepared by dissolving 3.3 g (17 mmol) of 1-adamantanecarbonyl chloride in 30 mL of dichloromethane. Thereafter, the mixture was stirred at 40° C. for 20 hours. After completing the reaction, the reaction solution was washed with water and a saturated aqueous sodium chloride solution, and the organic layer was dried over anhydrous magnesium sulfate. Thereafter, the residue obtained by concentrating the organic layer in vacuo was purified by silica gel column chromatography (developing solvent: dichloromethane/MeOH=12/1 (volume ratio)) to obtain 3.3 g of a compound (B1-1) (yield 49%).

$^1$H-NMR data of the compound (B1-1) thus obtained are shown below:

$^1$H-NMR (CDCl$_3$) δ: 1.63-1.93 (m, 15H), 3.20 (m, 2H, CH$_2$), 6.00 (m, 1H, CH), 7.67-7.83 (m, 15H)

Example 2

Synthesis of Compound (B1-2)

A compound represented by the following formula (B1-2) was obtained (2.7 g, yield 45%) in a similar manner to Example 1 except that a compound represented by the following formula (m-3) was used in place of 1-adamantanecarbonyl chloride used in Example 1.

$^1$H-NMR data of the compound (B1-2) thus obtained are shown below:

$^1$H-NMR (CDCl$_3$) δ: 1.00 (s, 6H, CH$_3$), 1.25 (s, 3H, CH$_3$), 1.70 (m, 1H, CH), 1.93 (m, 2H, CH), 2.16 (m, 1H, CH), 3.20 (m, 2H, CH$_2$), 6.00 (m, 1H, CH), 7.67-7.83 (m, 15H)

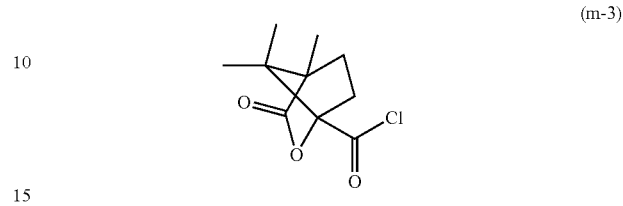

(m-3)

Example 3

Synthesis of Compound (B1-3)

A compound represented by the following formula (B1-3) was synthesized according to the following scheme.

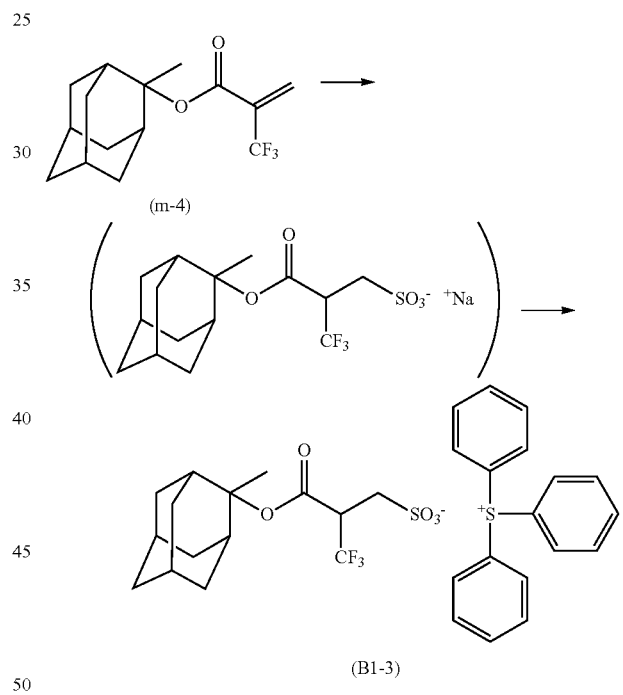

(B1-3)

Into a 500 mL eggplant shaped flask were charged 4.5 g (15.6 mmol) of the compound (m-4), 2.1 g (20.3 mmol) of NaHSO$_3$, 75 mL of MeOH, 25 mL of CH$_3$CN and 75 mL of H$_2$O, and the mixture was stirred at 60° C. for 10 hours under a nitrogen atmosphere. After completing the reaction, the reaction solution was concentrated in vacuo until the volume of the reaction liquid was reduced to approximately ¼ of the initial volume. To this, 3.7 g (12.5 mmol) of triphenylsulfonium chloride and 100 mL of dichloromethane were added, and the mixture was stirred at room temperature for 5 hours. After completing the reaction, only the organic layer was recovered, and the recovered organic layer was washed three times with 30 mL of water and dried over anhydrous magnesium sulfate. Thereafter, the residue obtained by concentrating the organic layer in vacuo was purified by silica gel column chromatography (developing solvent: dichloromethane/MeOH=12/1 (volume ratio)) to obtain 3.8 g of a compound (B1-3) (yield 38%).

¹H-NMR data of the compound (B1-3) thus obtained are shown below:

¹H-NMR (CDCl₃) δ: 1.35 (s, 3H, CH₃), 1.63-1.93 (m, 14H), 3.12 (m, 2H, CH₂), 3.90 (m, 1H, CH), 7.67-7.83 (m, 15H)

Example 4

Synthesis of Compound (B1-4)

A compound represented by the following formula (B1-4) was obtained (2.1 g, yield 34%) in a similar manner to Example 3 except that a compound represented by the following formula (m-5) was used in place of the compound (m-4) used in Example 3.

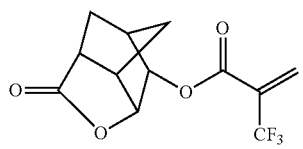

(m-5)

¹H-NMR data of the compound (B1-4) thus obtained are shown below:

¹H-NMR (CDCl₃) δ: 1.65-1.81 (m, 2H), 2.06 (m, 2H), 2.59 (m, 2H), 3.20 (m, 3H), 3.90 (m, 1H, CH), 4.60 (m, 2H), 7.67-7.83 (m, 15H)

Example 5

Synthesis of Compound (B1-5)

A compound represented by the following formula (B1-5) was obtained (0.8 g, yield 19%) in a similar manner to Example 3 except that a compound represented by the following formula (m-6) was used in place of the compound (m-4) used in Example 3.

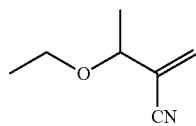

(m-6)

¹H-NMR data of the compound (B1-5) thus obtained are shown below:

¹H-NMR (CDCl₃) δ: 1.28 (s, 3H, CH₃), 3.20 (m, 2H, CH₂), 3.62 (m, 1H, CH), 4.21 (m, 2H, CH₂), 7.67-7.83 (m, 15H)

Example 6

Synthesis of Compound (B1-6)

A compound represented by the following formula (B1-6) was obtained (1.2 g, yield 24%) in a similar manner to Example 1 except that 3-bromo-4,4,4-trifluorobutan-2-ol (a compound represented by the following formula (m-7)) was used in place of 2-bromo-3,3,3-trifluoropropan-1-ol used in Example 1 and 1-cyclohexylcarbonyl chloride (a compound represented by the following formula (m-8)) was used in place of 1-adamantanecarbonyl chloride used in Example 1.

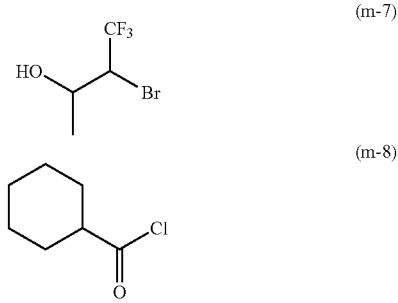

¹H-NMR data of the compound (B1-6) thus obtained are shown below:

¹H-NMR (CDCl₃) δ: 1.25 (m, 3H), 1.40-1.98 (m, 10H, CH₂), 2.27 (m, 1H, CH), 3.09 (m, 1H, CH), 5.97 (m, 1H, CH), 7.67-7.83 (m, 15H)

Example 7

Synthesis of Compound (B1-7)

Into a 300 mL reaction flask were charged 5.0 g (20.4 mmol) of o-(trifluoromethyl)benzenesulfonyl chloride and 30 mL of dioxane, and the mixture was cooled to 0° C. under a nitrogen atmosphere. To this was slowly added dropwise an aqueous solution prepared by dissolving 1.0 g (24.5 mmol) of NaOH in 60 mL of H₂O. Thereafter, the mixture was stirred at 0° C. for 1 hour. After completing the reaction, a 1 N aqueous HCl solution was slowly added dropwise to the reaction solution so that the pH of the reaction solution was reached 7. Subsequently, the reaction solution was concentrated in vacuo until the volume of the reaction solution was reduced to about ⅔ of the initial volume. To this, 8.5 g (28.6 mmol) of triphenylsulfonium chloride and 150 mL of dichloromethane were added, and the mixture was stirred at room temperature for 5 hours. After completing the reaction, only the organic layer was recovered, and the recovered organic layer was washed three times with 40 mL of water and dried over anhydrous magnesium sulfate. Thereafter, the residue obtained by concentrating the organic layer in vacuo was purified by silica gel column chromatography (developing solvent: dichloromethane/MeOH=12/1 (volume ratio)) to obtain 3.2 g of a compound (B1-7) (yield 32%).

¹H-NMR data of the compound (B1-7) thus obtained are shown below:

¹H-NMR (CDCl₃) δ: 7.32-7.40 (m, 3H), 7.62-7.83 (m, 16H)

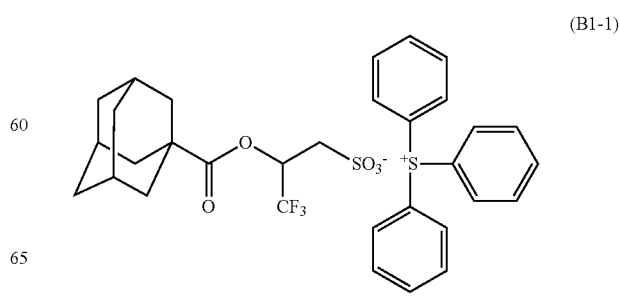

(B1-1)

-continued (B1-2)
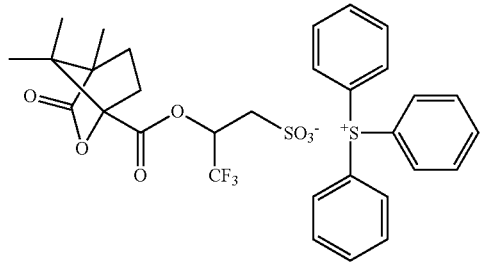

(B1-3)
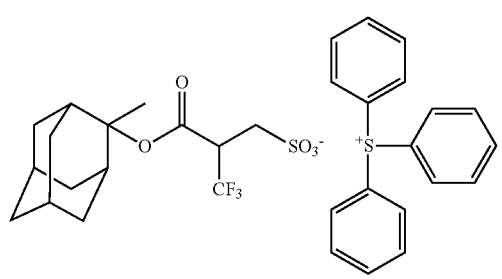

(B1-4)
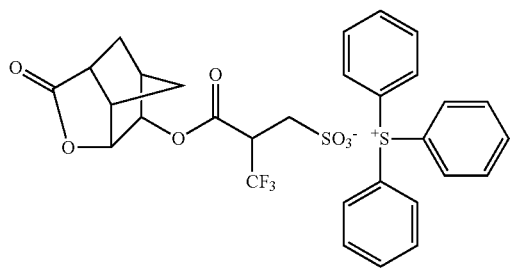

(B1-5)
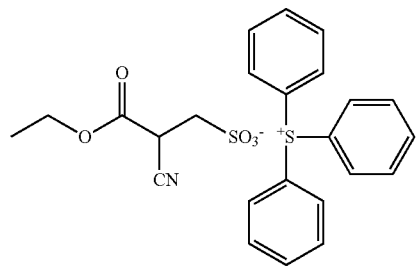

(B1-6)
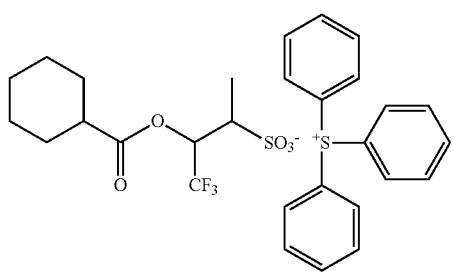

-continued (B1-7)
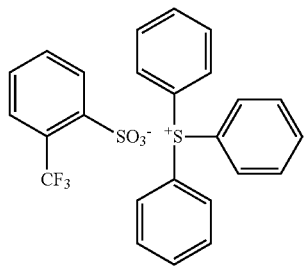

Synthesis of Polymer (A)

Synthesis Example 1

Synthesis of Polymer (A-1)

A monomer solution was prepared by dissolving 14.2 g (35 mol %) of the following compound (m-9), 9.0 g (15 mol %) of the following compound (m-10) and 26.8 g (50 mol %) of the following compound (m-11) in 100 g of 2-butanone, and further dissolving 1.98 g of 2,2′-azobisisobutyronitrile therein. Into a 500 mL three-neck flask was charged 50 g of 2-butanone, and purging with a nitrogen gas was executed for 30 min. After the purging with nitrogen, 2-butanone in the three-neck flask was heated to 80° C. with stirring. Then, the monomer solution prepared above was added dropwise over 3 hours using a dropping funnel. After completing the dropwise addition, the mixture was stirred at 80° C. for another 3 hours. After completing the polymerization, the polymerization reaction liquid was cooled to no greater than 30° C. with water. Then, the polymerization reaction liquid was poured into 1,000 g of methanol to deposit a white powder, and thereafter the white powder was filtered off. The filtered white powder was washed twice with 200 g of methanol (each) in a slurry state, and then the powder was filtered off. Then, the polymer as a white powder thus obtained was dried at 50° C. for 17 hours to obtain a polymer (A-1) (recovered amount 38 g, yield 76%). The polymer (A-1) had an Mw of 7,300 and an Mw/Mn of 1.42. In addition, the result of $^{13}$C-NMR analysis indicated that the proportions of the structural unit derived from the compound (m-9): the structural unit derived from the compound (m-10): the structural unit derived from the compound (m-11) were 36:11:53 (mol %).

(m-9)
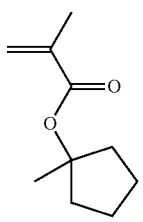

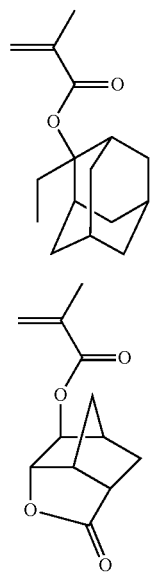

(m-10)

(m-11)

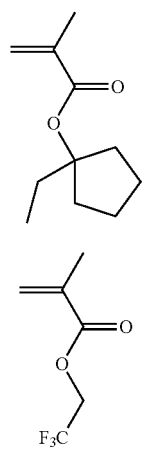

(m-12)

(m-13)

Synthesis of Polymer (D)

Synthesis Example 2

Synthesis of Polymer (D-1)

A monomer solution was prepared by dissolving 21.5 g (70 mol %) of the following compound (m-12) and 8.5 g (30 mol %) of the following compound (m-13) in 30 g of 2-butanone, and further charging 1.38 g of 2,2'-azobisisobutyronitrile thereinto. Separately, 30 g of 2-butanone was charged into a 200 mL three-neck flask, and purging with a nitrogen gas was executed for 30 min. After the purging with nitrogen, 2-butanone in the three-neck flask was heated to 80° C. with stirring. Then, the monomer solution prepared above was added dropwise over 3 hours using a dropping funnel. After completing the dropwise addition, the mixture was stirred at 80° C. for another 3 hours. After completing the polymerization, the polymerization reaction liquid was cooled to no greater than 30° C. with water. Then, the polymerization reaction liquid was concentrated through vacuum distillation until the mass thereof was reduced to 45 g. Thereafter, the concentrated polymerization reaction liquid was poured into 225 g of a mixed liquid of methanol/water (1/1 volume ratio) to deposit a white powder, and the white powder was separated through decantation. The separated white powder was washed twice with 45 g of methanol (each) in a slurry state, and then the powder was filtered off. The polymer as a white powder thus obtained was dried at 50° C. for 17 hours to obtain a polymer (D-1) (recovered amount 13.5 g, yield 45%). The polymer (D-1) had an Mw of 7,700 and an Mw/Mn of 1.44. In addition, the result of $^{13}$C-NMR analysis indicated that the proportions of the structural unit derived from the compound (m-12): the structural unit derived from the compound (m-13) were 69:31 (mol %).

Preparation of Radiation-Sensitive Resin Composition

Components used in the preparation of the radiation-sensitive resin composition are shown below:

(B) Acid Generating Agent

Compound (I):

The compounds (B1-1) to (B1-7) synthesized in Examples 1 to 7 as described hereinbefore Other Acid Generating Agent:

Compounds represented by the following formulae (B2-1) to (B2-5)

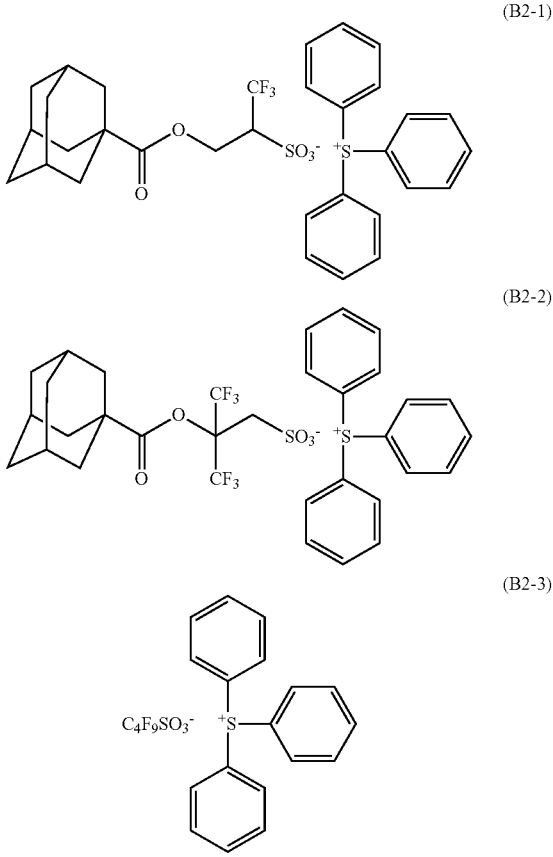

-continued

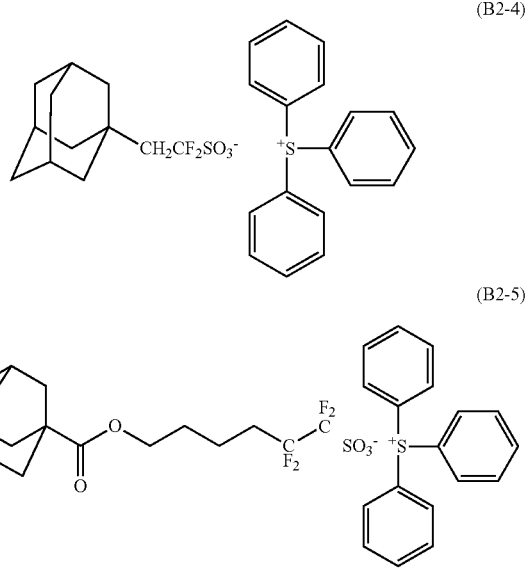

(B2-4)

(B2-5)

(C) Acid Diffusion Control Agent
C-1: 2-phenylbenzimidazole (a compound represented by the following formula (C-1))
C-2: N-t-amyloxycarbonyl-4-hydroxypiperidine (a compound represented by the following formula (C-2))
C-3: triphenylsulfonium salicylate (a compound represented by the following formula (C-3))
C-4: triphenylsulfonium 10-camphorsulfonate (a compound represented by the following formula (C-4))

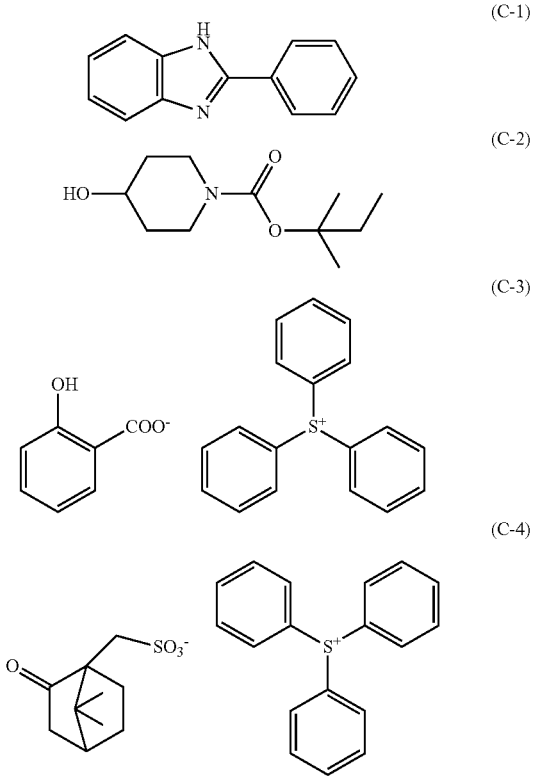

(C-1)

(C-2)

(C-3)

(C-4)

(E) Solvent
E-1: propylene glycol monomethyl ether acetate
E-2: cyclohexanone
E-3: γ-butyrolactone Example 8

After 100 parts by mass of the polymer (A-1) as the polymer (A), 5 parts by mass of (B1-1) and 6 parts by mass of (B2-4) as the acid generating agent (B), 1.2 parts by mass of (C-1) as the acid diffusion control agent (C), 3 parts by mass of the polymer (D-1) as the polymer (D), as well as 2,400 parts by mass of (E–1), 1,000 parts by mass of (E-2) and 30 parts by mass of (E-3) as the solvent (E) were mixed, the mixture was filtered through a filter with a pore size of 0.05 μm to obtain a radiation-sensitive resin composition (J-1).

Examples 9 to 20 and Comparative Examples 1 to 6

Radiation-sensitive resin compositions (J-2) to (J-13) and (CJ-1) to (CJ-6) were obtained in a similar manner to Example 8 except that the type and amount of each component were as specified in Table 1.
Evaluations The following evaluations were made using each radiation-sensitive resin composition prepared above. The results of the evaluations are also shown in Table 1.
LWR Performance A composition for forming a resist underlayer film (ARC66, manufactured by Nissan Chemical Industries, Ltd.) was coated on the surface of a 12 inch silicon wafer using a spin-coating method. Then, the composition was baked at 205° C. for 60 sec to provide a resist underlayer film having a film thickness of 105 nm. Each radiation-sensitive resin composition prepared above was spin-coated on the resist film, and prebaked at 100° C. for 50 sec, followed by cooling at 23° C. for 30 sec to provide a resist film having a film thickness of 90 nm. Subsequently, an exposure was carried out using an ArF immersion scanner (S610C, manufactured by NIKON) through a mask for projecting a bright field pattern having a line of 40 nm and a pitch of 80 nm, under optical conditions involving NA of 1.30, a ratio of outer σ/inner σ being 0.977/0.782, with Dipole and v-polarization illumination. Subsequently, PEB was carried out using a hot plate at 105° C. for 50 sec. Then, a puddle development was carried out using a 2.38% by mass aqueous tetramethylammonium hydroxide solution as a developer solution for 10 sec with a GP nozzle of a development unit, followed by rinsing with ultra pure water. Spin drying was conducted at 2,000 rpm for 15 sec to obtain a substrate having a resist pattern provided thereon. In this process, an exposure dose at which a resist pattern with a line of 40 nm and a pitch of 80 nm was formed was designated as an optimal exposure dose, and this optimal exposure dose was regarded as sensitivity (mJ/cm$^2$). The resist pattern with a line of 40 nm and a pitch of 80 nm resolved at the optimal exposure dose was observed from above the pattern using a SEM (CG4000, manufactured by Hitachi, Ltd.) to measure line widths at arbitrary ten points, and the degree of distribution of the measurements expressed in terms of the 3 Sigma was defined as LWR (nm). Smaller LWR values indicate more favorable uniformity of the line widths of the pattern after the development.

TABLE 1

| Composition | Com-posi-tion | (A) Polymer type | (A) Polymer amount (parts by mass) | (B) Acid generating agent type | (B) Acid generating agent amount (parts by mass) | (C) Acid diffusion controller type | (C) Acid diffusion controller amount (parts by mass) | (D) Polymer type | (D) Polymer amount (parts by mass) | (E) Solvent type | (E) Solvent amount (parts by mass) | Evaluation result sensitivity (mJ/cm$^2$) | Evaluation result LWR (nm) |
|---|---|---|---|---|---|---|---|---|---|---|---|---|---|
| Example 8 | J-1 | A-1 | 100 | B1-1/B2-4 | 5/6 | C-1 | 1.2 | D-1 | 3 | E-1/E-2/E-3 | 2,400/1,000/30 | 30 | 2.8 |
| Example 9 | J-2 | A-1 | 100 | B1-1/B2-4 | 5/6 | C-2 | 1.2 | D-1 | 3 | E-1/E-2/E-3 | 2,400/1,000/30 | 30 | 2.9 |
| Example 10 | J-3 | A-1 | 100 | B1-1/B2-4 | 4/5 | C-3 | 2.3 | D-1 | 3 | E-1/E-2/E-3 | 2,400/1,000/30 | 29 | 2.7 |
| Example 11 | J-4 | A-1 | 100 | B1-1/B2-4 | 4/5 | C-4 | 2.3 | D-1 | 3 | E-1/E-2/E-3 | 2,400/1,000/30 | 28 | 2.8 |
| Example 12 | J-5 | A-1 | 100 | B1-1/B2-5 | 4/5 | C-4 | 2.3 | D-1 | 3 | E-1/E-2/E-3 | 2,400/1,000/30 | 26 | 2.9 |
| Example 13 | J-6 | A-1 | 100 | B1-2/B2-4 | 5.2/6 | C-2 | 1.2 | D-1 | 3 | E-1/E-2/E-3 | 2,400/1,000/30 | 28 | 2.8 |
| Example 14 | J-7 | A-1 | 100 | B1-3/B2-4 | 4/5 | C-4 | 2.3 | D-1 | 3 | E-1/E-2/E-3 | 2,400/1,000/30 | 29 | 2.7 |
| Example 15 | J-8 | A-1 | 100 | B1-4/B2-5 | 4.4/5 | C-2 | 1.2 | D-1 | 3 | E-1/E-2/E-3 | 2,400/1,000/30 | 26 | 2.7 |
| Example 16 | J-9 | A-1 | 100 | B1-5/B2-4 | 5/5 | C-2 | 1.2 | D-1 | 3 | E-1/E-2/E-3 | 2,400/1,000/30 | 32 | 2.9 |
| Example 17 | J-10 | A-1 | 100 | B1-6/B2-3 | 5/5 | C-1 | 1.2 | D-1 | 3 | E-1/E-2/E-3 | 2,400/1,000/30 | 28 | 2.8 |
| Example 18 | J-11 | A-1 | 100 | B1-7/B2-3 | 4.2/5 | C-1 | 1.2 | D-1 | 3 | E-1/E-2/E-3 | 2,400/1,000/30 | 29 | 2.6 |
| Example 19 | J-12 | A-1 | 100 | B1-3/B2-4/B2-5 | 4/3/2 | C-4 | 2.3 | D-1 | 3 | E-1/E-2/E-3 | 2,400/1,000/30 | 26 | 2.7 |
| Example 20 | J-13 | A-1 | 100 | B1-3/B2-4/B2-5 | 4/3/2 | C-3 | 2.3 | D-1 | 3 | E-1/E-2/E-3 | 2,400/1,000/30 | 26 | 2.6 |
| Comparative Example 1 | CJ-1 | A-1 | 100 | B2-1/B2-4 | 5/6 | C-2 | 1.2 | D-1 | 3 | E-1/E-2/E-3 | 2,400/1,000/30 | 24 | 3.4 |
| Comparative Example 2 | CJ-2 | A-1 | 100 | B2-2/B2-4 | 5.2/6 | C-2 | 1.2 | D-1 | 3 | E-1/E-2/E-3 | 2,400/1,000/30 | 23 | 3.8 |
| Comparative Example 3 | CJ-3 | A-1 | 100 | B2-2 | 9 | C-4 | 2.3 | D-1 | 3 | E-1/E-2/E-3 | 2,400/1,000/30 | 28 | 3.5 |
| Comparative Example 4 | CJ-4 | A-1 | 100 | B2-3/B2-4 | 4/5 | C-3 | 2.3 | D-1 | 3 | E-1/E-2/E-3 | 2,400/1,000/30 | 22 | 3.6 |
| Comparative Example 5 | CJ-5 | A-1 | 100 | B2-4/B2-5 | 7/2 | C-2 | 1.2 | D-1 | 3 | E-1/E-2/E-3 | 2,400/1,000/30 | 21 | 3.8 |
| Comparative Example 6 | CJ-6 | A-1 | 100 | B2-3/B2-5 | 6/3 | C-1 | 1.2 | D-1 | 3 | E-1/E-2/E-3 | 2,400/1,000/30 | 22 | 3.7 |

As is clear from the results shown in Table 1, the resist pattern formed from the radiation-sensitive resin composition exhibited superior LWR performance.

INDUSTRIAL APPLICABILITY

The radiation-sensitive resin composition and the resist pattern-forming method according to the present invention enable a resist pattern with reduced LWR to be formed. The acid generator according to the present invention can be suitably used as a component of a radiation-sensitive resin composition and improve the LWR performance thereof. The compound of the present invention can be suitably used as the acid generator. Therefore, these can be suitably used in lithography steps of processes for production of semiconductors and the like, in which further progress of miniaturization is expected in the future.

What is claimed is:

1. A radiation-sensitive resin composition, comprising:
a polymer comprising a structural unit which comprises an acid-labile group; and
at least one acid generator comprising a first acid generator represented by formula (2), and optionally a second acid generator other than the first acid generator:

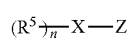
(2)

wherein in the formula (2):
Z represents a group represented by formula (1-1) or (1-2);
X represents OCO—;
n is an integer of 1;
R$^5$ represents a cycloalkyl group, or a group comprising a lactone structure;

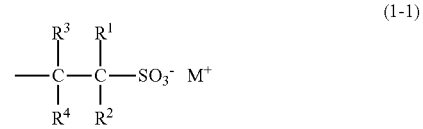
(1-1)

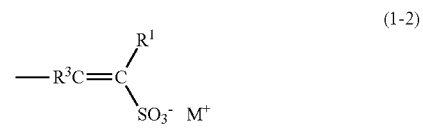
(1-2)

wherein in the formulae (1-1) and (1-2):
R$^1$ and R$^2$ each independently represent a hydrogen atom or a methyl group;
R$^3$ represents a cyano group;
R$^4$ represents a hydrogen atom; and
M$^+$ represents a monovalent radiation-degradable onium cation.

2. The radiation-sensitive resin composition according to claim 1, wherein the radiation-degradable onium cation is a sulfonium cation or an iodonium cation.

3. The radiation-sensitive resin composition according to claim 1, wherein the structural unit that includes an acid-labile group is represented by formula (4):

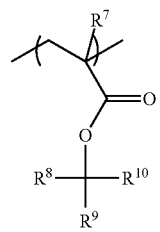

(4)

wherein in the formula (4),
$R^7$ represents a hydrogen atom, a fluorine atom, a methyl group or a trifluoromethyl group;
$R^8$ represents a monovalent hydrocarbon group having 1 to 20 carbon atoms;
$R^9$ and $R^{10}$ each independently represent a monovalent linear hydrocarbon group having 1 to 10 carbon atoms or a monovalent alicyclic hydrocarbon group having 3 to 20 carbon atoms; and
$R^9$ and $R^{10}$ optionally taken together represent an alicyclic structure having 3 to 20 carbon atoms together with the carbon atom to which $R^9$ and $R^{10}$ bond.

4. A resist pattern-forming method, comprising:
applying the radiation-sensitive resin composition according to claim 1 on a substrate to form the resist film;
exposing the resist film; and
developing the exposed resist film.

5. The radiation-sensitive resin composition according to claim 1, wherein a content of the first acid generator in the at least one acid generator is in a range of 25% by mass to 90% by mass.

6. The radiation-sensitive resin composition according to claim 1, wherein a content of the first acid generator in the at least one acid generator is in a range of 30% by mass to 70% by mass.

7. The radiation-sensitive resin composition according to claim 1, further comprising an acid diffusion controller.

8. The radiation-sensitive resin composition according to claim 1, further comprising a fluorine atom-containing polymer other than the polymer.

9. The radiation-sensitive resin composition according to claim 1, wherein Z represents a group represented by formula (1-1).

10. The radiation-sensitive resin composition according to claim 9, wherein $R^1$ and $R^2$ each represent a hydrogen atom.

11. A compound represented by formula (2):

(2)

wherein in the formula (2):
Z represents a group represented by formula (1-1) or (1-2);
X represents OCO—;
n is an integer of 1;
$R^5$ represents a cycloalkyl group, or a group comprising a lactone structure;

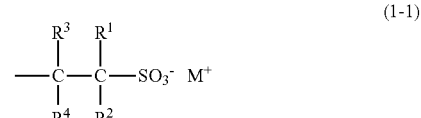

(1-1)

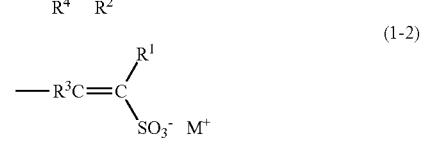

(1-2)

wherein in the formulae (1-1) and (1-2):
$R^1$ and $R^2$ each independently represent a hydrogen atom or a methyl group;
$R^3$ represents a cyano group;
$R^4$ represents a hydrogen atom; and
$M^+$ represents a monovalent radiation-degradable onium cation.

12. The compound according to claim 11, wherein Z represents a group represented by formula (1-1).

13. The compound according to claim 12, wherein $R^1$ and $R^2$ each represent a hydrogen atom.

* * * * *